(12) United States Patent
Tanaka et al.

(10) Patent No.: US 12,269,021 B2
(45) Date of Patent: Apr. 8, 2025

(54) ARTIFICIAL PROTEIN CATALYST

(71) Applicant: Glytech, Inc., Kyoto (JP)

(72) Inventors: Katsunori Tanaka, Niiza (JP); Kenward Vong, Wako (JP); Taiji Shimoda, Kyoto (JP)

(73) Assignee: Glytech, Inc., Kyoto (JP)

(*) Notice: Subject to any disclaimer, the term of this patent is extended or adjusted under 35 U.S.C. 154(b) by 574 days.

(21) Appl. No.: 17/612,780

(22) PCT Filed: May 18, 2020

(86) PCT No.: PCT/JP2020/019593
§ 371 (c)(1),
(2) Date: Nov. 19, 2021

(87) PCT Pub. No.: WO2020/241340
PCT Pub. Date: Dec. 3, 2020

(65) Prior Publication Data
US 2022/0241765 A1 Aug. 4, 2022

(30) Foreign Application Priority Data

May 24, 2019 (JP) ................................ 2019-097739

(51) Int. Cl.
*B01J 31/22* (2006.01)
*A61K 33/00* (2006.01)
(Continued)

(52) U.S. Cl.
CPC .............. *B01J 31/22* (2013.01); *A61K 33/00* (2013.01); *A61K 33/24* (2013.01); *A61K 33/242* (2019.01);
(Continued)

(58) Field of Classification Search
CPC ...... A61K 31/366; A61K 33/00; A61K 33/24; A61K 33/242; A61K 33/244; A61K 47/42;
(Continued)

(56) References Cited

U.S. PATENT DOCUMENTS

2021/0353652 A1* 11/2021 Vincent ................ A61K 47/545

FOREIGN PATENT DOCUMENTS

| CN | 103463643 A | 12/2013 | |
|---|---|---|---|
| DE | 102016125516 A1 * | 6/2018 | ............ B01J 31/003 |

(Continued)

OTHER PUBLICATIONS

Machine translation of Grimm et al. (Year: 2018).*
(Continued)

*Primary Examiner* — Brian A McCaig
(74) *Attorney, Agent, or Firm* — Myers Bigel, P.A.

(57) ABSTRACT

[Problem] To provide a novel artificial protein catalyst that enables the protection of a catalyst from substances in vivo and has potential usefulness in therapeutic in vivo synthetic chemistry.
[Solution] Provided is a complex of a protein and a catalyst selected from a metal catalyst or organic catalyst. In the complex according to the present invention, the protein is a protein having a hydrophobic pocket in the three-dimensional structure thereof, and the catalyst is housed in the hydrophobic pocket so that the catalyst is not or substantially not exposed to a hydrophilic environment.

20 Claims, 13 Drawing Sheets

(51) Int. Cl.

| | |
|---|---|
| A61K 33/24 | (2019.01) |
| A61K 33/242 | (2019.01) |
| A61K 33/244 | (2019.01) |
| A61K 47/42 | (2017.01) |
| A61K 47/54 | (2017.01) |
| A61P 43/00 | (2006.01) |
| B01J 23/46 | (2006.01) |
| C07K 14/765 | (2006.01) |
| C07K 14/79 | (2006.01) |
| G01N 21/78 | (2006.01) |
| G01N 31/10 | (2006.01) |

(52) U.S. Cl.
CPC ............ *A61K 33/244* (2019.01); *A61K 47/42* (2013.01); *A61K 47/54* (2017.08); *A61P 43/00* (2018.01); *B01J 23/462* (2013.01); *C07K 14/765* (2013.01); *C07K 14/79* (2013.01); *G01N 21/78* (2013.01); *G01N 31/10* (2013.01)

(58) Field of Classification Search
CPC ........ A61K 47/54; A61K 47/61; A61K 47/66; A61P 43/00; B01J 23/462; B01J 31/003; B01J 31/165; B01J 31/22; B01J 31/2208; B01J 31/2278; B01J 2231/543; B01J 2231/546; B01J 2531/0291; B01J 2531/18; B01J 2531/821; B01J 2540/64; B01J 2540/66; B01J 2540/68; C07K 14/765; C07K 14/79
See application file for complete search history.

(56) References Cited

FOREIGN PATENT DOCUMENTS

| JP | 6327547 B2 | 4/2018 | | |
|---|---|---|---|---|
| WO | 2008096760 A1 | 8/2008 | | |
| WO | WO-2015183987 A1 | * 12/2015 | ............ | A61K 31/44 |
| WO | 2017002918 A1 | 1/2017 | | |

OTHER PUBLICATIONS

Bertucci et al. "Aqueous Biphasic Hydroformylation Catalysed by Protein—Rhodium Complexes" Advanced Synthesis and Catalysis, 344(5):556-562 (2002).
Extended European Search Report corresponding to European Patent Application No. 20812900.7 (9 pages) (dated May 26, 2023).
Kokubo et al. "The Bovine Serum Albumin-2-Phenylpropane-1, 2-diolatodioxo—osium (V) Complex as an Enantioselective Catalyst for cis -Hydroxylation of Alkenes" Journal of the Chemical Society, Chemical Communications, 14:769-770 (1983).
Mahammed et al. "Albumin-Conjugated Corrole Metal Complexes: Extremely Simple Yet Very Efficient Biomimetic Oxidation Systems" Journal of the American Chemical Society, 127(9):2883-2887 (2005).
Marchetti et al. "A protein—rhodium complex as an efficient catalyst for two—phase olefin hydroformylation" Tetrahedron Letters, 41(19):3717-3720 (2000).
Okamoto et al. "A cell-penetrating artificial metalloenzyme regulates a gene switch in a designer mammalian cell" Nature Communications, 9(1943):1-7 (2018).
Tanaka et al. "Unlocking the therepeutic potential of artificial metalloenzymes" Proceedings of the Japan Academy, Series B, Physical and Biological Sciences, 96(3):79-94 (2020).
Tang et al. "Bovine serum albumin-cobalt(II) Schiff base complex hybrid: an efficient artificial metalloenzyme for enantioselective sulfoxidation using hydrogen peroxide" Dalton Transactions, 45(19):8061-8072 (2016).
Bray, Thomas L., et al., "Bright insights into palladium-triggered local chemotherapy", Chemical Science, 9(37), 2018, 7354-7361.

Clavadetscher, Jessica, et al., "Copper Catalysis in Living Systems and In Situ Drug Synthesis", Angewandte Chemie, 128(50), 2016, 15891-15895.
Clavadetscher, Jessica, et al., "In-Cell Dual Drug Synthesis by Cancer-Targeting Palladium Catalysts", Angewandte Chemie, 129(24), 2017, 6968-6972.
Destito, Paolo, et al., "Hollow nanoreactors for Pd-catalyzed Suzuki—Miyaura coupling and O-propargyl cleavage reactions in bio-relevant aqueous media", Chemical Science, 10(9), 2019, 2598-2603.
Eda, Shohei, et al., "Biocompatibility and therapeutic potential of glycosylated albumin artificial metalloenzymes", Nature Catalysis, 2, 2019, 780-792.
Eda, Shohei, et al., "In Vivo Transition Metal Catalyzed Reactions: Therapeutic In Vivo Synthetic Chemistry", 35th Symposium on Medicinal Chemistry, Abstracts (partial English machine translation included), 2017, 68.
Eda, Shohei, et al., "Protein-Bound Metathesis Catalyst for Therapeutic In Vivo Synthetic Chemistry", The 98th Annual Spring Meeting of the Chemical Society of Japan, Lecture Notes DVD (including partial English machine translation), 2018.
Li, Jie, et al., "Palladium-triggered deprotection chemistry for protein activation in living cells", Nature Chemistry, 6, 2014, 352-361.
Liu, Yiliu, et al., "Catalytically Active Single-Chain Polymeric Nanoparticles: Exploring Their Functions in Complex Biological Media", Journal of the American Chemical Society, 140(9), 2018, 3423-3433.
Miller, Miles A., et al., "Nano-palladium is a cellular catalyst for in vivo chemistry", Nature Communications, 8 (Article No. 15906), 2017, 1-13.
Ogura, Akihiro, et al., "Next-generation glycocluster for achieving pattern recognition in living system", Journal of the Organic Synthetic Chemistry Society, 77(2) (including English abstract and partial English translation), 2019, 163-172.
Perez-Lopez, Ana M., et al., "Gold-Triggered Uncaging Chemistry in Living Systems", Angewandte Chemie International Edition, 56(41), 2017, 12548-12552.
Rebelein, Johannes G., et al., "In vivo catalyzed new-to-nature reactions", Current Opinion in Biotechnology, 53, 2018, 106-114.
Streu, Craig, et al., "Ruthenium-Induced Allylcarbamate Cleavage in Living Cells", Angewandte Chemie International Edition, 45(34), 2006, 5645-5648.
Tomas-Gamasa, Maria, et al., "Transition metal catalysis in the mitochondria of living cells", Nature Communications, 7(Article No. 12538), 2016, 1-10.
Tonga, Gulen Yesilbag, et al., "Supramolecular regulation of bioorthogonal catalysis in cells using nanoparticle-embedded transition metal catalysts", Nature Chemistry, 7(7), 2015, 597-603.
Tsubokura, Kazuki, et al., "In Vivo Gold Complex Catalysis within Live Mice", Angewandte Chemie International Edition, 56(13), 2017, 3579-3584.
Unciti-Broceta, Asier, et al., "Synthesis of polystyrene microspheres and functionalization with Pd0 nanoparticles to perform bioorthogonal organometallic chemistry in living cells", Nature Protocols, 7, 2012, 1207-1218.
Vidal, Cristian, et al., "Concurrent and orthogonal gold(I) and ruthenium(II) catalysis inside living cells", Nature Communications, 9(Article No. 1913), 2018, 1-9.
Volker, Timo, et al., "Progress towards Bioorthogonal Catalysis with Organometallic Compounds", Angewandte Chemie International Edition, 53(39), 2014, 10536-10540.
Vong, Kenward, et al., "An artificial metalloenzyme biosensor can detect ethylene gas in fruits and Arabidopsis leaves", Nature Communications, 10(Article No. 5746), 2019, 1-15.
Weiss, Jason T., et al., "Extracellular palladium-catalysed dealkylation of 5-fluoro-1-propargyl-uracil as a bioorthogonally activated prodrug approach", Nature Communications, 5(Article No. 3277), 2014, 1-9.
Yusop, Rahimi M., et al., "Palladium-mediated intracellular chemistry", Nature Chemistry, 3, 2011, 239-243.

(56) References Cited

OTHER PUBLICATIONS

Sauer et al. "A Highly Active Biohybrid Catalyst for Olefin Metathesis in Water: Impact of a Hydrophobic Cavity in a β Barrel Protein" ACS Catalysis, 5:7519-7522 (2015).
Leenders et al. "Transition metal catalysis in confined spaces" Chem. Soc. Rev. 44:433-448 (2015).

* cited by examiner

ARTIFICIAL PROTEIN CATALYST

TECHNICAL FIELD

The present invention relates to a novel artificial protein catalyst.

BACKGROUND ART

Currently, attempts related to "in vivo synthetic chemical treatments" utilizing catalysts are being investigated. The concept of in vivo synthetic chemical treatment is to introduce a material or reagent without activity or toxicity into the body, and activating the said material or reagent at a particular location in the body with a catalyst to allow effects to be expressed. In such circumstances, interests related to the development of a new catalyst that is applicable to therapeutic applications are increasing (Non-Patent Literature 1).

One obstacle in the development of such catalyst is the protection of a catalyst from in vivo substances. For example, it is known that metal catalysts (metalloenzymes) such as gold (Au), palladium (Pd), ruthenium (Ru), and the like are quickly inactivated when exposed to thiol-containing glutathione (GSH) that exists in cells in the range of 0.5-10 mM or in blood plasma in the range of about 2-20 μM.

At this point, in many research, investigation of catalyst reaction has only been performed in cells or in models other than mammals such as zebrafish via any of artificial metal enzymes or metal catalyst complexes (Non-Patent Literatures 2-17).

CITATION LIST

Non-Patent Literatures

[Non-Patent Literature 1] Rebelein, J. G.; Ward, T. R. Curr. Opin. Biotechnol. 2018, 53, 106-114.

[Non-Patent Literature 2] Miller, M. A.; Askevold, B.; Mikula, H.; Kohler, R. H.; Pirovich, D.; Weissleder, R. Nat. Commun. 2017, 8, 15906.

[Non-Patent Literature 3] Clavadetscher, J.; Hoffmann, S.; Lilienkampf, A.; Mackay, L.; Yusop, R. M.; Rider, S. A.; Mullins, J. J.; Bradley, M. Angew. Chem. Int. Ed. Engl. 2016, 55, 15662-15666.

[Non-Patent Literature 4] Clavadetscher, J.; Indrigo, E.; Chankeshwara, S. V.; Lilienkampf, A.; Bradley, M. Angew. Chem. Int. Ed. Engl. 2017, 56, 6864-6868.

[Non-Patent Literature 5] Weiss, J. T.; Dawson, J. C.; Macleod, K. G.; Rybski, W.; Fraser, C.; Torres-Sanchez, C.; Patton, E. E.; Bradley, M.; Carragher, N. O.; Unciti-Broceta, A. Nat. Commun. 2014, 5, 3277.

[Non-Patent Literature 6] Perez-Lopez, A. M.; Rubio-Ruiz, B.; Sebastian, V.; Hamilton, L.; Adam, C.; Bray, T. L.; Irusta, S.; Brennan, P. M.; Lloyd-Jones, G. C.; Sieger, D.; Santamaria, J.; Unciti-Broceta, A. Angew. Chem. Int. Ed. Engl. 2017, 56, 12548-12552.

[Non-Patent Literature 7] Bray, T. L.; Salji, M.; Brombin, A.; Perez-Lopez, A. M.; Rubio-Ruiz, B.; Galbraith, L. C. A.; Patton, E. E.; Leung, H. Y.; Unciti-Broceta, A. Chem. Sci. 2018, 9, 7354-7361.

[Non-Patent Literature 8] Liu, Y.; Pujals, S.; Stals, P. J. M.; Paulohrl, T.; Presolski, S. I.; Meijer, E. W.; Albertazzi, L.; Palmans, A. R. A. J. Am. Chem. Soc. 2018, 140, 3423-3433.

[Non-Patent Literature 9] Li, J.; Yu, J.; Zhao, J.; Wang, J.; Zheng, S.; Lin, S.; Chen, L.; Yang, M.; Jia, S.; Zhang, X.; Chen, P. R. Nat. Chem. 2014, 6, 352-361.

[Non-Patent Literature 10] Vidal, C.; Tomas-Gamasa, M.; Destito, P.; Lopez, F.; Mascarenas, J. L. Nat. Commun. 2018, 9, 1913.

[Non-Patent Literature 11] Destito, P.; Sousa-Castillo, A.; Couceiro, J. R.; Lopez, F.; Correa-Duarte, M. A.; Mascarenas, J. L. Chem. Sci. 2019, 10, 2598-2603.

[Non-Patent Literature 12] Tonga, G. Y.; Jeong, Y.; Duncan, B.; Mizuhara, T.; Mout, R.; Das, R.; Kim, S. T.; Yeh, Y.-C.; Yan, B.; Hou, S.; Rotello, V. M. Nat. Chem. 2015, 7, 597-603.

[Non-Patent Literature 13] Streu, C.; Meggers, E. Angew. Chem. Int. Ed. Engl. 2006, 45, 5645-5648.

[Non-Patent Literature 14] Volker, T.; Dempwolff, F.; Graumann, P. L.; Meggers, E. Angew. Chem. Int. Ed. Engl. 2014, 53, 10536-10540.

[Non-Patent Literature 15] Tomas-Gamasa, M.; Martinez-Calvo, M.; Couceiro, J. R.; Mascarenas, J. L. Nat. Commun. 2016, 7, 12538.

[Non-Patent Literature 16] Yusop, R. M.; Unciti-Broceta, A.; Johansson, E. M. V.; Sanchez-Martin, R. M.; Bradley, M. Nat. Chem. 2011, 3, 239-243.

[Non-Patent Literature 17] Unciti-Broceta, A.; Johansson, E. M. V.; Yusop, R. M.; Sanchez-Martin, R. M.; Bradley, M. Nat. Protoc. 2012, 7, 1207-1218.

SUMMARY OF THE INVENTION

Problems to be Solved by the Invention

The object of the present invention is to provide a novel artificial protein catalyst that allows the protection of a catalyst from in vivo substances and has potential usefulness for in vivo synthetic chemical treatment.

Means for Solving the Problems

Human serum albumin (HSA) is a 66.5 kDa protein that exists abundantly in blood plasma, and it is known to have a half-life in the serum of about 19 days (Peters, T., Jr. Adv. Protein Chem. 1985, 37, 161-245.). HSA is known to be a carrier protein for various hormones, fatty acids, and low-molecular agents, and multiple major and minor binding sites for numerous kinds of ligands have been confirmed in HSA (Ghuman, J.; Zunszain, P. A.; Petitpas, I.; Bhattacharya, A. A.; Otagiri, M.; Curry, S. J. Mol. Biol. 2005, 353, 38-52.).

In order to design biocompatible artificial protein catalysts, the present inventors selected HSA as the protein, and considered accommodating a metal catalyst in the hydrophobic binding pocket of HSA. It was found that by using a metal catalyst ruthenium as the catalyst, when the metal catalyst was fixed to the albumin drug binding site I known for binding (interaction) with a coumarin derivative (such as warfarin), it was possible to protect the catalytic activity of the bound ruthenium under in vitro conditions even in the presence of 20 mM GSH, thus coming to complete the present invention.

In other words, the present invention encompasses the following characteristics:

[1] A complex of a protein and a catalyst selected from metal catalysts or organic catalysts, wherein said protein is a protein that has a hydrophobic pocket within its three-dimensional structure, and said complex accommodates said catalyst in said hydrophobic pocket so that said catalyst is not exposed or not substantially exposed to the hydrophilic environment.

[2] The complex according to [1], wherein said protein is a natural or artificial protein.

[3] The complex according to [1] or [2], wherein said protein is selected from the group consisting of human serum albumin (HSA), immunoglobulin G (IgG), immunoglobulin A (IgA), transferrin, antitrypsin, haptoglobin, α1-acidic glycoprotein, Myoferlin, Trk receptor, estrogen receptor, and folate receptor.

[4] The complex according to any of [1] to [3], wherein said metal catalyst is selected from the group consisting of a boron catalyst, a magnesium catalyst, an aluminum catalyst, a silicon catalyst, a calcium catalyst, a scandium catalyst, a titanium catalyst, a vanadium catalyst, a chromium catalyst, a manganese catalyst, an iron catalyst, a cobalt catalyst, a nickel catalyst, a copper catalyst, a zinc catalyst, an yttrium catalyst, a zirconium catalyst, a niobium catalyst, a molybdenum catalyst, a ruthenium catalyst, a rhodium catalyst, a palladium catalyst, a silver catalyst, an indium catalyst, a tin catalyst, a barium catalyst, a hafnium catalyst, a tungsten catalyst, a rhenium catalyst, an osmium catalyst, an iridium catalyst, a platinum catalyst, a gold catalyst, and a lanthanoid Lewis acid catalyst.

[5] The complex according to [4], wherein said lanthanoid Lewis acid catalyst is selected from the group consisting of an ytterbium catalyst, a lanthanum catalyst, a cerium catalyst, a samarium catalyst, an europium catalyst, a gadolinium catalyst, a terbium catalyst, a thulium catalyst, and a lutetium catalyst.

[6] The complex according to any of [1] to [5], wherein
said protein is a human serum albumin, and
said catalyst is a metal catalyst.

[7] The complex according to [6], wherein said metal catalyst is a ruthenium catalyst.

[8] The complex according to [6] or [7], wherein said hydrophobic pocket of human serum albumin is the albumin drug binding site I (drug site I).

[9] The complex according to any of [6] to [8], wherein said metal catalyst is bound to the said hydrophobic pocket via a ligand against human serum albumin.

[10] The complex according to [9], wherein said ligand is selected from the group consisting of warfarin, azapropazone, acenocoumarol, phenylbutazone, salicylate salt, indomethacin, phenytoin, tolbutamide, chlorpropamide, iophenoxate, iodipamide, sulfadimethoxine, phenprocoumon, glibenclamide, sulfathiazole, tenoxicam, camptothecin, balzidendeazi, andelleratan, diadelleal, diadellealtan, prodan, bilirubin, eicosanoid, and carboxy-methyl-propyl-furanpropanoate (uremic toxin), as well as coumarin.

[11] The complex according to [9] or [10], wherein said metal catalyst is bound to the said hydrophobic pocket via a linker bound to said ligand.

[12] The complex according to [11], wherein said linker is an alkyl chain or a polyethylene glycol (PEG) chain having amino and carboxyl groups on both ends.

[13] The complex according to [12], wherein said linker is a $C_1$-$C_3$ alkyl or a PEG chain with a polymerization degree of 1-3.

[14] The complex according to any of [1] to [13], wherein the surface of said protein is modified so as to interact with a target site in vivo.

[15] The complex according to [14], wherein said modification is a modification by a sugar chain.

[16] The complex according to any of [1] to [13], wherein said protein further comprises a portion that interacts with a target site in vivo.

[17] The complex according to [14] or [15], wherein said protein is human serum albumin.

[18] A composition comprising the complex according to any of [1] to [17].

[19] The composition according to [18], which is a pharmaceutical composition further comprising a pharmaceutically acceptable carrier.

[20] The composition according to [19], which is used in combination with a prodrug that can be activated by said complex.

[21] The composition according to [19], further comprising a prodrug that can be activated by said complex.

[22] The composition according to [19], which is employed for selectively tagging particular cells.

[23] The composition according to [22], which is administered in combination with a chemical substance that is tagged to said cells.

[24] The composition according to [18], which is used as a biosensor.

[25] The composition according to [18], which is used as a biosensor for detecting ethylene.

[26] A pharmaceutical composition comprising a prodrug, wherein
said prodrug can be activated by the complex according to any of [1] to [17], and
said pharmaceutical composition is used in combination with the complex according to any of [1] to [17].

[27] A combination medicine comprising
a first agent comprising the complex according to any of [1] to [17], and
a second agent comprising a prodrug that can be activated by said complex.

Those skilled in the art will be able to recognize that an invention of any combination of one or more characteristics of the present invention described above is also encompassed by the scope of the present invention.

Effects of the Invention

According to the present invention, a novel artificial protein catalyst that allows the protection of a catalyst from in vivo substances is provided.

DESCRIPTION OF EMBODIMENTS

Figure 1:
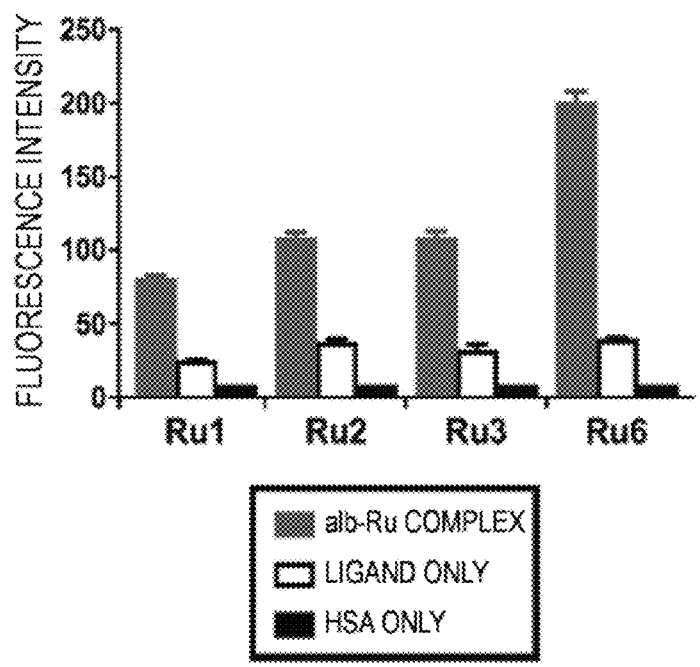
FIG. 1 shows the fluorescence assay result of the product obtained by the reaction between ruthenium catalysts Ru1-3, 6 and HSA.

The present invention relates to a novel artificial protein catalyst. Specifically, the artificial protein catalyst according to the present invention is a complex of a protein and a catalyst selected from metal catalysts or organic catalysts (hereinafter also referred to as "the complex of the present invention.")

The complex of the present invention can be characterized by a configuration that accommodates a catalyst within the hydrophobic pocket of a protein that has said hydrophobic pocket within its three-dimensional structure, so that the catalyst is not exposed or not substantially exposed to the hydrophilic environment. In other words, the complex of the present invention can protect the catalyst from in vivo substances by avoiding exposure or substantial exposure of the catalyst to the hydrophilic environment. The complex of the present invention may accommodate the catalyst in only one out of the hydrophobic pockets present in the protein, or may accommodate the catalyst in multiple (or all) pockets.

The complex of the present invention can also be characterized by having a configuration that avoids exposure or substantial exposure of the catalyst to the hydrophilic environment, and meanwhile the catalyst may still promote the target reaction while having the aforementioned configuration. In other words, in a preferred embodiment, the complex of the present invention may protect the catalyst from in vivo substances while exerting the desired activity in vivo.

In the present invention, "the catalyst is not substantially exposed to the hydrophilic environment" refers to that exposure to the hydrophilic environment is permitted to the extent that protection of the catalyst from the hydrophilic environment is recognized. "Protection of the catalyst from the hydrophilic environment is recognized" refers to that in comparison to when a free catalyst is exposed to an in vivo environment, the activity of the catalyst accommodated in the complex of the present invention is maintained for a longer period under the same environment, and for example can be evaluated by metabolic turnover (TON). The extent that the exposure is permitted may change depending on the type of catalyst used, or the type of protein used in combination, etc.

In one embodiment of the present invention, "the catalyst is not substantially exposed to the hydrophilic environment" means that the relative solvent accessible surface area (SASA) of the catalyst when accommodated in the hydrophobic pocket of the protein is 5.0 or less, preferably 4.0 or less, more preferably 3.5 or less, more preferably 3.0 or less, more preferably 2.5 or less, more preferably 2.0 or less, more preferably, 1.5 or less, more preferably 1.0 or less, more preferably 0.9 or less, more preferably 0.8 or less, more preferably 0.7 or less, more preferably 0.6 or less, more preferably 0.5 or less, more preferably 0.4 or less, more preferably 0.3 or less, more preferably 0.2 or less, or more preferably 0.1 or less.

In another embodiment of the present invention, "the catalyst is not substantially exposed to the hydrophilic environment" means that 50% or more, preferably 55% or more, more preferably 60% or more, more preferably 65% or more, more preferably 70% or more, more preferably 75% or more, more preferably 80% or more, more preferably 85% or more, more preferably 90% or more, more preferably 95% or more, more preferably 96% or more, more preferably 97% or more, more preferably 98% or more, or more preferably 99% or more of the total surface area of the catalyst is accommodated internally in the hydrophobic pocket of the protein. Alternatively, "the catalyst is not substantially exposed to the hydrophilic environment" means that the area of the catalyst exposed to the hydrophilic environment is 50% or less, preferably 45% or less, more preferably 40% or less, more preferably 35% or less, more preferably 30% or less, more preferably 25% or less, more preferably 20% or less, more preferably 15% or less, more preferably 10% or less, more preferably 5% or less, more preferably 4% or less, more preferably 3% or less, more preferably 2% or less, or more preferably 1% or less of the total surface area of the catalyst.

The protein that can be used for the complex of the present invention is not limited as long as it has one or more hydrophobic pockets that allow accommodation of the catalyst, and natural or artificial proteins can be employed. Artificial proteins include a mutated protein where a mutation is artificially introduced into a part of a natural protein.

In one embodiment, the protein used for the complex of the present invention is a protein where a ligand that binds to or interacts with any of the hydrophobic pockets of the protein is easily obtained. Such a protein may be preferable in that is facilitates the complexation of the catalyst via the ligand.

In a specific embodiment, the protein used for the complex of the present invention is a protein selected from human serum albumin (HSA), immunoglobulin G (IgG), immunoglobulin A (IgA), transferrin, antitrypsin, haptoglobin, α1-acidic glycoprotein, and the like. These proteins are thought to be suitable for drug delivery system since they are proteins that can move freely in blood. In yet another specific embodiment, the protein used for the complex of the present invention is a protein selected from Myoferlin, Trk receptor, estrogen receptor, folate receptor, and the like. Since these proteins are known to be greatly expressed in cancer cells, it is thought that by coordinating ligands and metals thereto, a complex that can directly kill cancer could be manufactured.

The organic or metal catalyst that can be used for the complex of the present invention is not particularly limited, and can be arbitrary selected by those skilled in the art. In one embodiment, the organic or metal catalyst that can be used for the complex of the present invention is one that has the activity to change a given prodrug to an active form.

For example, the organic catalyst used for the complex of the present invention can include, but is not limited to, proline derivatives, phase transfer catalysts based on quaternary ammonium salt derivatives, thiourea derivatives, N-heterocyclic carbene derivatives obtained from thiazolium salts or imidazolium salts, cyclic ketone derivatives, 4-dimethylaminopyridine derivatives, secondary amines such as amino acids, and the like.

For example, the metal catalyst used for the complex of the present invention can include, but is not limited to, a boron catalyst, a magnesium catalyst, an aluminum catalyst, a silicon catalyst, a calcium catalyst, a scandium catalyst, a titanium catalyst, a vanadium catalyst, a chromium catalyst, a manganese catalyst, an iron catalyst, a cobalt catalyst, a nickel catalyst, a copper catalyst, a zinc catalyst, an yttrium catalyst, a zirconium catalyst, a niobium catalyst, a molybdenum catalyst, a ruthenium catalyst, a rhodium catalyst, a palladium catalyst, a silver catalyst, an indium catalyst, a tin catalyst, a barium catalyst, a hafnium catalyst, a tungsten catalyst, a rhenium catalyst, an osmium catalyst, an iridium catalyst, a platinum catalyst, a gold catalyst, a lanthanoid Lewis acid catalyst, and the like. Moreover, said lanthanoid Lewis acid catalyst can also include, but is not limited to, an ytterbium catalyst, a lanthanum catalyst, a cerium catalyst, a samarium catalyst, an europium catalyst, a gadolinium catalyst, a terbium catalyst, a thulium catalyst, a lutetium catalyst, and the like.

Means for accommodating the catalyst in the hydrophobic pocket of the protein can include, for example, a means for binding the catalyst into the hydrophobic pocket via a ligand that interacts with or binds to said hydrophobic pocket. In such a case, a linker of peptides, hydrocarbon chains, PEGs, and the like can be appropriately employed for linking the ligand and the catalyst (such as a metal catalyst). The length of the linker used should be a length such that the catalyst is accommodated within the hydrophobic pocket and is not exposed or not substantially exposed to the hydrophilic environment. In other words, when the linker used is too long in relation to the hydrophobic pocket, the ligand that interacts therewith, and the size of the catalyst used, there is a possibility that when the catalyst is bound to the hydrophobic pocket via the linker and the ligand, the catalyst is not housed within the hydrophobic pocket, all or a portion thereof is exposed from the hydrophobic pocket to the hydrophilic environment, and sufficient protection from the hydrophilic environment could not be obtained.

Another means for accommodating the catalyst in the hydrophobic pocket of the protein can include, for example, applying maleimide or succinimide to the side chain functional group of cysteine or lysine (thiol group and amino group, respectively) present within or in the vicinity of the hydrophobic pocket of the protein to allow activation and covalent binding with the catalyst.

Yet another means for accommodating the catalyst in the hydrophobic pocket of the protein can include introducing a mutation in a particular position of the amino acid sequence that configures the hydrophobic pocket to introduce a double bond or an azide to allow metathesis or click reaction and covalent binding with the catalyst (Young T S, Ahmad I, Brock A, Schultz P G., Expanding the genetic repertoire of the methylotrophic yeast *Pichia pastoris*., Biochemistry. 2009. 48 (12): 2643-53.; Wang L, Schultz PG., Expanding the genetic code., Angew Chem Int Ed Engl. 2004. 44 (1): 34-66.). In such a case, a catalyst having a linker such as a peptide or PEG can be used as the catalyst (such as a metal catalyst).

In one embodiment, the complex of the present invention is modified to interact with the in vivo target site. As a result, the complex of the present invention can be guided to an in vivo desired site or can target the desired site. In relation to this, "interacts with a target site in vivo" may mean accumulates or typically binds to the target site with significantly strong directionality compared to other in vivo sites. In the present invention, the target site may be a particular organ or a particular cytoma etc.

Such modifications can include e.g. glycosylation. For example, it is known that by employing an asparagine-linked sugar chain (N-linked sugar chain) for protein modification, the directionality towards a particular organ changes depending on the number of clusters and/or the number of bindings of its sugar chain (Tanaka, K., et al., Angew. Chem. Int. Ed., 49, 8195-8200 (2010); Latypova, L., et al., Adv. Sci., 1600394 (2017); Ogura, A., et al., Chem. Commun., 54, 8693-8696 (2018); Taichi, M., et al., Adv. Sci., 1700147 (2017)). For example, it is known that a sugar chain having a sialic acid on its terminal swiftly reaches the liver, or a sugar chain having a galactose on its terminal the intestinal tract. Accordingly, by modifying the complex of the present invention with the appropriate sugar chain structure and number of sugar chains depending on the selected in vivo target site, a complex with enhanced directionality towards said target site can be obtained.

In one embodiment, for example, multiple (such as 5-30) sugar chains having sialic acid, galactosamine, galactose, or mannose that interact with various types of cancer at the non-reducing terminal can be employed as the glycosylation. In an alternative embodiment, sugar chains having fucose can be employed as the glycosylation. In the aforementioned embodiment, the multiple sugar chains to be modified may be the same or multiple types, and the size of each sugar chain can be in the range of from 1 to 25 sugars.

In another embodiment, for example, multiple (such as 5-30) sugar chains having sialic acid, galactosamine, galactose, or mannose that selectively transfers into particular organs such as liver, pancreas, intestinal tract, gallbladder, bladder, or brain at the non-reducing terminal can be employed as the glycosylation. In the aforementioned embodiment, the multiple sugar chains to be modified may be of the same or multiple types, and the size of each sugar chain may be in the range of from 1 to 25 sugars.

The modification site is typically the protein surface of said complex. The method for glycosylating a particular site of the protein surface is well-known to those skilled in the art, and any method may be employed. In the present invention, for example, glycosylation can be introduced to the protein surface by the click reaction described in International Publication No. 2008/096760, Japanese Patent No. 6327547, International Publication No. 2017/002918, and the like.

In another embodiment, the complex of the present invention further comprises a portion that interacts with a target site in vivo. In relation to this, "interacts with the target site" may mean accumulates or typically binds to the target site with significantly strong directionality compared to other sites. In the present invention, the target site may be a particular organ or a particular cytoma etc.

In the present invention, "a portion that interacts with a target site in vivo" may be an antibody or a fragment thereof, a peptide ligand or a fragment thereof, DNA or RNA, or pNA (peptide nucleic acid) or a fragment thereof, and the like. In relation to this, "a portion that interacts with a target site in vivo" may for example be manufactured as a fusion protein with the protein employed for the complex, or the protein employed for the complex and "a portion that interacts with a target site in vivo" may be separately prepared and then bound (e.g. covalently bound) by means well-known to those skilled in the art.

In a specific embodiment, the present invention relates to an artificial metal enzyme (artificial metalloenzyme; ArM) which is a complex of a protein and a metal catalyst. In a preferred embodiment, the ArM of the present invention is a complex of HSA and a metal catalyst, wherein said complex is characterized in that it accommodates the metal catalyst in the hydrophobic pocket of HSA so that the metal catalyst is not exposed or not substantially exposed to the hydrophilic environment.

In this embodiment, the metal catalyst used together with HSA can be appropriately selected by those skilled in the art for example according to the type of prodrug subject to activation etc. In one embodiment of the present invention, the metal catalyst used together with HSA is ruthenium.

In this embodiment, the hydrophobic pocket of HSA that accommodates the metal catalyst is not particularly limited, and one hydrophobic pocket may accommodate the metal catalyst or multiple hydrophobic pockets may accommodate the metal catalyst. The hydrophobic pocket of HSA can include the albumin drug binding site I and the albumin drug binding site II. In one embodiment, the complex of the present invention accommodates the metal catalyst in the albumin drug binding site I of HSA.

In this embodiment, the metal catalyst can be accommodated in the hydrophobic pocket of HSA by linking the metal catalyst with a ligand against HSA, and then binding the metal catalyst within the hydrophobic pocket via said ligand. The ligand that can be used for this purpose may change depending on the hydrophobic pocket that accommodates the metal catalyst. For example, when accommodating the metal catalyst in the albumin drug binding site I of HSA, said ligand can be selected from warfarin, azapropazone, acenocoumarol, phenylbutazone, salicylate salt, indomethacin, phenytoin, tolbutamide, chlorpropamide, iophenoxate, iodipamide, sulfadimethoxine, phenprocoumon, glibenclamide, sulfathiazole, tenoxicam, camptothecin, balzidendeazi, andelleratan, diadelleal, diadellealtan, prodan, bilirubin, eicosanoid, and carboxy-methyl-propyl-furanpropanoate (uremic toxin), as well as coumarin. Alternatively, when accommodating the metal catalyst in the albumin drug binding site II of HSA, said ligand can be selected from diazepam, ketoprofen, chlofibrate, ibuprofen, iopanoate, azide deoxythymidine, flufenamate, ethacrynate, naproxen, flurbiprofen, ciclofen, benoxaprofen, flucloxacillin, chlorothiazide, pirprofen, propofol, isoflurane, dansylsarcosine, dansylglycine, alkylaminocoumarin acetic acid, hydroxyflavone, L-tryptophan, medium chain fatty acid anion (such as octanoate), L-thyroxine, chloride ion, iodoacetic acid, indoxyl sulfate, and hippuric acid (urotoxin). In one embodiment of the present invention, the hydrophobic pocket of HSA is the drug binding site I, and a coumarin derivative, e.g. 7-dimethylamino coumarin is used as the ligand in order to accommodate ruthenium in the aforementioned site.

The linking between the metal catalyst and said ligand may be performed via a linker. As the linker that can be used for this purpose, an alkyl chain or a polyethylene glycol (PEG) chain etc. having an amino group and a carboxy group on both ends can be typically employed. Specifically, alkyl chain linkers can include, for example, —NH—$(CH_2)_x$—CO— (wherein x is an integer and is not limited as long as it does not inhibit the target linker function, and for example can be an integer between 1-15), —NH—$(CH_2CH_2O)_y$—$CH_2$—CO— (wherein y is an integer and is not limited as long as it does not inhibit the target linker function, and for example can be an integer between 1-15), or —NH—$(CH_2CH_2O)_z$—$CH_2CH_2$—CO— (wherein z is an integer and is not limited as long as it does not inhibit the target linker function, and for example can be an integer between 1-15), and the like.

When a linker is employed for linking the metal catalyst and said ligand, it should be noted that the length of the linker used is a length such that the metal catalyst is accommodated within the hydrophobic pocket of HSA and is not exposed or not substantially exposed to the hydrophilic environment. For example, when accommodating ruthenium in the albumin drug binding site I of HSA employing coumarin or a derivative thereof (such as 7-dimethylamino coumarin, 7-diethylamino coumarin (DEAC)) as the ligand, "not substantially exposed to the hydrophilic environment" may be that the area of ruthenium exposed to the hydrophilic environment is 40% or less, and preferably 35% or less of the total surface area of ruthenium. Alternatively, "not substantially exposed to the hydrophilic environment" may be that the SASA of ruthenium when accommodated in the albumin drug binding site I of HSA is 3.0 or less, and preferably 1.0 or less. Moreover, an exemplary linker used in this case is —NH—$(CH_2CH_2O)_y$—$CH_2$—CO—, wherein y may be an integer from 1 to 6, and preferably an integer from 1 to 3.

In one embodiment, in the ArM of the present invention which is a complex of HSA and a metal catalyst, the surface of HSA is modified with a sugar chain. The content of the glycosylation may change depending on the in vivo target. The modification position on the HSA surface is not particularly limited as long as introduction of a sugar chain is possible, and an example can include the lysine residue at position 30 on the HSA surface.

The complex of the present invention can activate a prodrug in vivo depending on the type of the catalyst accommodated in the aforementioned complex. Preferably, the complex of the present invention, depending on the type of the catalyst accommodated in the aforementioned complex, is accumulated at a particular position in vivo to allow activation of the prodrug selective to the aforementioned position.

Accordingly, in another aspect, the present invention relates to a composition comprising the complex of the present invention.

In one embodiment, the composition of the present invention is a pharmaceutical composition that is used in combination with a prodrug that can be activated by the complex of the present invention. In the aforementioned embodiment, the pharmaceutical composition of the present invention may be a single dosage form further comprising a pharmaceutically acceptable carrier, and depending on the case a prodrug that can be activated by the complex of the present invention. Prodrugs that can be activated by the complex of the present invention that can be used in the present invention can include e.g. various anticancer agents, and specifically, but is not limited thereto, mitomycin C, doxorubicin, taxol, endoxifen, and the like can be exemplified.

In another embodiment, the pharmaceutical composition of the present invention is in a form of a combination medicine wherein the complex of the present invention and a prodrug that can be activated by the aforementioned complex are provided as separate agents. In the combination medicine of the present invention, a first agent comprising the complex of the present invention and a second agent comprising a prodrug that can be activated by the aforementioned complex can be administered to the subject at same or different times.

In another aspect, the composition of the present invention relates to a pharmaceutical composition comprising a prodrug that can be activated by the complex of the present invention and any pharmaceutically acceptable carrier, and the aforementioned pharmaceutical composition can be characterized by being used in combination with the complex of the present invention.

In one embodiment, the pharmaceutical composition of the present invention can be employed for selectively tagging particular cells in vivo. In the present invention, "tagging" refers to employing a non-toxic chemical substance that may be intrinsic or extrinsically administered and can destroy cell function (such as an adherence inhibitor) or can elicit immunological response, in order to tag a target cell. Such a chemical substance may be an in vivo or ex vivo chemical substance that is converted from an inactive form to an active form by any metal catalyst, or an in vivo or ex vivo chemical substance that is enhanced in its function by any metal catalyst. Such a method in therapeutic application is termed selective cell tagging (SeCT), and in contrast to conventional chemotherapy that directly removes cancer cells with a highly cytotoxic agent, it is expected to indirectly induce target cell (such as cancer cell) death without significantly damaging the surrounding tissue. For example, in the Examples herein, a possibility is shown that the binding of cRGD-propargyl ester (cRGD-PE) against integrins expressed on the cancer cell surface is enhanced by the complex of the present invention, and metastasis can be inhibited.

In another embodiment, the composition of the present invention can be employed as a biosensor. Specifically, in the complex of the present invention, by employing a metal catalyst, a linker having fluorescence per se and/or having fluorescence that is enhanced by binding with proteins such as albumin (such as a coumarin derivative), and a quencher that may depart by a reaction between the metal catalyst and the detection target substance, the complex or composition of the present invention can be designed as an appropriate biosensor according to the type of the detection target substance. In a specific embodiment of the present invention, the composition of the present invention is employed as a biosensor for detecting ethylene in plants.

Note that the terms used herein are to be employed to describe particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, should be construed as having meanings consistent with the meanings herein and in related technical fields, and shall not be construed as having idealized or excessively formal meanings.

Although terms such as first and second may be employed to express various elements, it should be recognized that these elements are not to be limited by these terms. These terms are employed solely for the purpose of discriminating one element from another, and for example, it is possible to describe the first element as the second element, and similarly to describe the first element as the second element without departing from the scope of the present invention.

The present invention will now be more specifically described by Examples. However, the present invention can be embodied by various embodiments, and shall not be construed as being limited to the Examples described herein.

EXAMPLES

Example 1

Manufacture of alb-Ru

In order to design a biocompatible artificial metal enzyme (ArM) that can prevent the exposure of the metal catalyst into the solvent (has a binding pocket), the drug binding site I (drug site I) of albumin (hydrophobic binding pocket as the pseudo-active site) was utilized. In order to accomplish the objective, a metal catalyst was fixed to the drug binding site I known for the binding (interaction) of coumarin derivatives (such as warfarin) (Ghuman, J.; Zunszain, P. A.; Petitpas, I.; Bhattacharya, A. A.; Otagiri, M.; Curry, S. J. Mol. Biol. 2005, 353, 38-52). Coumarin-Ru complexes Ru1-3, 6 having differing PEG linker lengths was employed for fixing the metal catalyst.

1. Preparation of Coumarin-Ru Complexes 1-1. General Procedure B

According to the following reaction scheme, coumarin-bound ruthenium complexes Ru1-3, 6 can be synthesized.

[Chemical Formula 1]

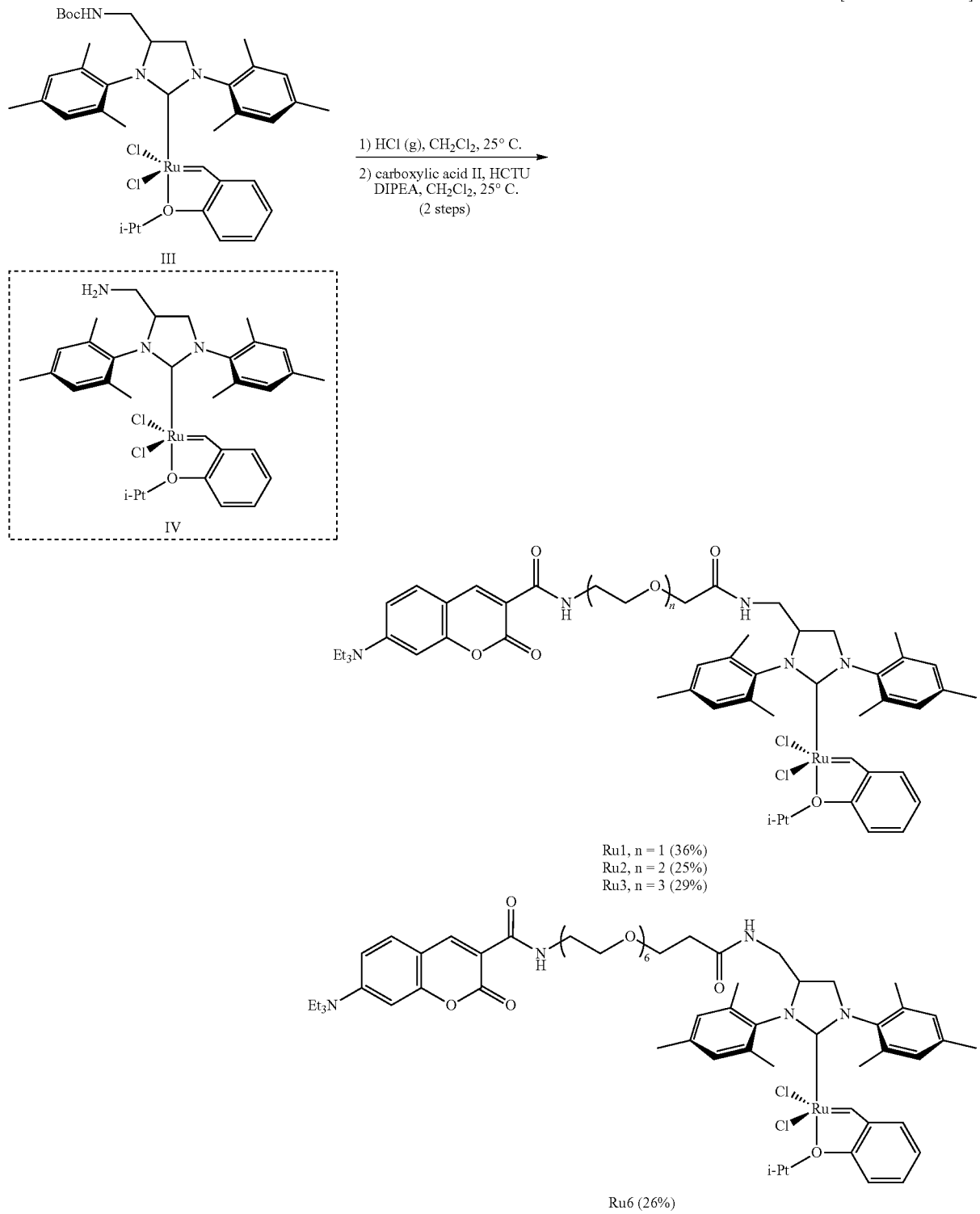

Ruthenium complex III is prepared according to a well-known technology (Lo, C.; Ringenberg, M. R.; Gnandt, D.; Wilson, Y.; Ward, T. R. ChemComm 2011, 47, 12065-12067; Kajetanowicz, A.; Chatterjee, A.; Reuter, R.; Ward, T. R. Catal. Lett. 2014, 144, 373-379; Zhao, J.; Kajetanowicz, A.; Ward, T. R. Org. Biomol. Chem. 2015, 13, 5652-5655). To a solution of ruthenium complex III (80.0 mg, 0.106 mmol) in dichloromethane (3 mL), hydrochloric acid gas is bubbled at 25° C. Hydrochloric acid gas is prepared by adding concentrated sulfuric acid dropwise to ammonium chloride. After stirring for 45 minutes, dichloromethane (1 mL) is added to the reactant with a syringe, and this is stirred at the same temperature. After another 15 minutes, the reactant is concentrated under reduced pressure to obtain amine IV, and this is used for the next reaction without purification.

In another flask, a solution of carboxylic acid IIa (1.1 equivalents) and a coupling agent HCTU (1.3 equivalents) dissolved in dichloromethane (1 mL) is stirred at 25° C. for 30 minutes. To this reactant, amine IV (1 equivalent) dissolved in dichloromethane (1 mL) was added, followed by N,N-diisopropylethylamine (10 equivalents) at the same temperature. After stirring for 6 hours, the reaction is stopped by adding 1 M HCl aqueous solution. The product is extracted three times with dichloromethane, the combined organic extract layer is washed with saturated sodium bicarbonate water and brine, dried (by sodium sulfate), and then concentrated under reduced pressure. The concentrated residue is purified by silica gel flash column chromatography, and coumarin-Ru complexes Ru1-3, 6 can be obtained.

1-2. Preparation of Coumarin-Ru Complex Ru1

According to general procedure B, after purification of the reactant obtained from ruthenium complex III (80.1 mg, 0.106 mmol), carboxylic acid IIa (42.4 mg, 0.117 mmol), HCTU (57.6 mg, 0.139 mmol), and N,N-diisopropylethylamine (137 mg, 1.06 mmol) by silica gel flash column chromatography (cyclohexane/EtOAc/CHCl$_3$/MeOH=40/40/15/5), the target coumarin-Ru complex Ru1 (37.7 mg, 35.6%) is obtained as a green solid.

$^1$H-NMR (400 MHz, CDCl$_3$, δ) 1.24-1.27 (m, 12H), 2.37-2.51 (br m, 18H), 3.47 (q, 4H, J=7.1 Hz), 3.53-3.71 (m, 6H), 3.79 (m, 1H), 3.93 (d, 1H, J=15.3 Hz), 3.99 (d, 1H, J=15.3 Hz), 4.05 (dd, 1H, J$_1$=J$_2$=10.0 Hz), 4.33 (dd, 1H, J$_1$=J$_2$=10.0 Hz), 4.75-4.84 (br m, 1H), 4.89 (sept, 1H, J=6.1 Hz), 6.50 (d, 1H, J=2.3 Hz), 6.66 (dd, 1H, J$_1$=2.3 Hz, J$_2$=9.1 Hz), 6.78 (d, 1H, J=7.7 Hz), 6.85 (dd, 1H, J$_1$=J$_2$=7.7 Hz), 6.91 (dd, 1H, J$_1$=1.7 Hz, J$_2$=7.7 Hz), 7.02 (s, overlapped, 2H), 7.04 (s, 1H), 7.07 (s, 1H), 7.42 (d, 1H, J=9.1 Hz), 7.48 (ddd, 1H, J$_1$=1.7 Hz, J$_2$=J$_3$=7.7 Hz), 8.67 (s, 1H), 9.09 (s, 1H), 16.50 (s. 1H);

HRMS (ESI) m/z 964.3355 (964.3359 calcd for C$_{50}$H$_{61}$ClN$_5$O$_6$Ru, [M-Cl]$^+$).

[Chemical Formula 2]

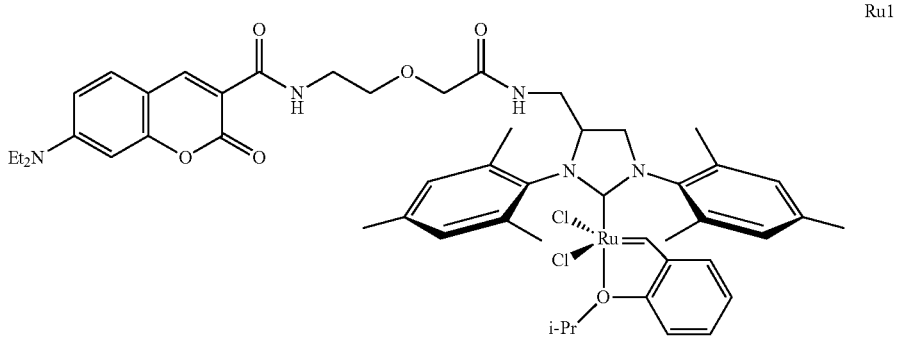

1-3. Preparation of Coumarin-Ru Complex Ru2

According to general procedure B, after purification of the reactant obtained from ruthenium complex III (80.1 mg, 0.106 mmol), carboxylic acid IIb (47.4 mg, 0.117 mmol), HCTU (57.1 mg, 0.138 mmol), and N,N-diisopropylethylamine (137 mg, 1.06 mmol) by silica gel flash column chromatography (cyclohexane/EtOAc/CHCl$_3$/MeOH=40/40/15/5), the target coumarin-Ru complex Ru2 (27.9 mg, 25.2%) was obtained as a green solid.

$^1$H-NMR (400 MHz, CDCl$_3$, δ) 1.22-1.26 (m, 12H), 2.26-2.46 (br m, 18H), 3.38-3.54 (m, 4H), 3.61-3.70 (m, 10H), 3.74-3.82 (m, 1H), 3.97 (s, 2H), 4.11 (dd, 1H, J$_1$=J$_2$=10.3 Hz), 4.28 (dd, 1H, J$_1$=J$_2$=10.3 Hz), 4.66-4.75 (br m, 1H), 4.88 (sept, 1H, J=6.1 Hz), 6.47 (d, 1H, J=2.3 Hz), 6.65 (dd, 1H, J$_1$=2.3 Hz, J$_2$=9.0 Hz), 6.77 (d, 1H, J=7.6 Hz), 6.83 (dd, 1H, J$_1$=J$_2$=7.6 Hz), 6.89 (dd, 1H, J$_1$=1.9 Hz, J$_2$=7.6 Hz), 6.98-7.01 (br m, 4H), 7.43 (d, 1H, J=9.0 Hz), 7.47 (ddd, 1H, J$_1$=1.9 Hz, J$_2$=J$_3$=7.6 Hz), 8.67 (s, 1H), 9.05 (s, 1H), 16.47 (s. 1H);

HRMS (ESI) m/z 1008.3613 (1008.3622 calcd for C$_{52}$H$_{65}$ClN$_5$O$_7$Ru, [M-Cl]$^+$).

[Chemical Formula 3]

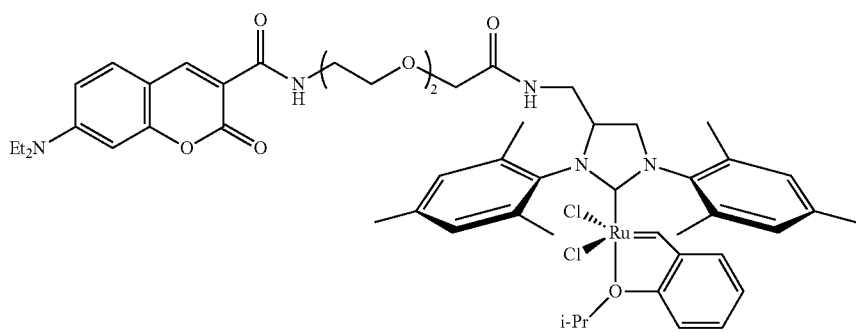

Ru2

1-4. Preparation of Coumarin-Ru Complex Ru3

According to general procedure B, after purification of the reactant obtained from ruthenium complex III (28.8 mg, 38.1 μmol), carboxylic acid IIc (18.9 mg, 42.0 μmol), HCTU (21.3 mg, 51.5 μmol), N,N-diisopropylethylamine (49.7 μg, 385 μmol) by silica gel flash column chromatography (cyclohexane/EtOAc/CHCl$_3$/MeOH=40/40/15/5), the target coumarin-Ru complex Ru3 (12.0 mg, 28.9%) was obtained as a green solid.

$^1$H-NMR (400 MHz, CDCl$_3$, δ) 1.22-1.28 (m, 12H), 2.34-2.44 (br m, 18H), 3.46 (q, 4H, J=7.2 Hz), 3.55-3.70 (m, 14H), 3.71-3.80 (m, 1H), 3.95 (s, 2H), 4.04 (dd, 1H, $J_1=J_2=10.7$ Hz), 4.27 (dd, 1H, $J_1=J_2=10.7$ Hz), 4.57-4.65 (m, 1H), 4.89 (sept, 1H, J=6.2 Hz), 6.47 (d, 1H, J=2.3 Hz), 6.65 (dd, 1H, $J_1=2.3$ Hz, $J_2=8.8$ Hz), 6.79 (d, 1H, J=7.7 Hz), 6.84 (dd, 1H, $J_1=J_2=7.6$ Hz), 6.89 (dd, 1H, $J_1=1.9$ Hz, $J_2=7.6$ Hz), 7.01-7.05 (br m, 4H), 7.42 (d, 1H, J=8.8 Hz), 7.47 (ddd, 1H, $J_1=1.9$ Hz, $J_2=J_3=7.6$ Hz), 8.67 (s, 1H), 8.98 (s, 1H), 16.47 (s. 1H);

HRMS (ESI) m/z 1088.3661 (1088.3648 calcd for $C_{54}H_{70}Cl_2N_5O_8Ru$, [M+H]$^+$).

[Chemical Formula 4]

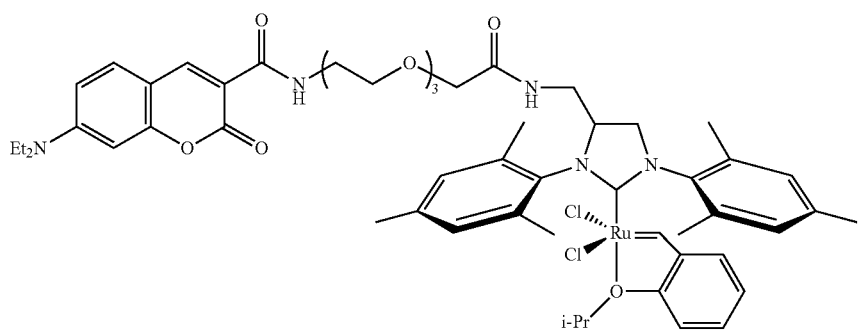

Ru3

1-5. Preparation of Coumarin-Ru Complex Ru6

According to general procedure B, after purification of ruthenium complex III (80.4 mg, 0.106 mmol), carboxylic acid IId (69.9 mg, 0.117 mmol), HCTU (57.5 mg, 0.139 mmol), N,N-diisopropylethylamine (137 mg, 1.06 mmol) by silica gel flash column chromatography (cyclohexane/EtOAc/CHCl$_3$/MeOH=20/20/55/5), the target coumarin-Ru complex Ru6 (34.4 mg, 26.3%) was obtained as a green solid.

$^1$H-NMR (400 MHz, CDCl$_3$, δ) 1.21-1.30 (m, 12H), 2.37-2.45 (br m, 18H), 3.45 (q, 4H, J=7.3 Hz), 3.56-3.68 (m, 31H), 3.99 (dd, 1H, $J_1=J_2=10.5$ Hz), 4.25 (dd, 1H, $J_1=J_2=10.5$ Hz), 4.53-4.62 (br m, 1H), 4.91 (sept, 1H, J=6.1 Hz), 6.49 (d, 1H, J=2.3 Hz), 6.64 (dd, 1H, $J_1=2.3$ Hz, $J_2=8.8$ Hz), 6.80 (d, 1H, J=7.6 Hz), 6.86 (dd, 1H, J=7.6 Hz), 6.90 (dd, 1H, $J_1=1.9$ Hz, $J_2=7.6$ Hz), 7.03-7.07 (br m, 4H), 7.42 (d, 1H, J=8.8 Hz), 7.48 (ddd, 1H, $J_1=1.9$ Hz, $J_2=J_3=7.6$ Hz), 8.68 (s, 1H), 9.00 (s, 1H), 16.47 (s. 1H);

HRMS (ESI) m/z 1234.4603 (1234.4593 calcd for $C_{61}H_{84}Cl_2N_5O_{11}Ru$, [M+H]$^+$).

[Chemical Formula 5]

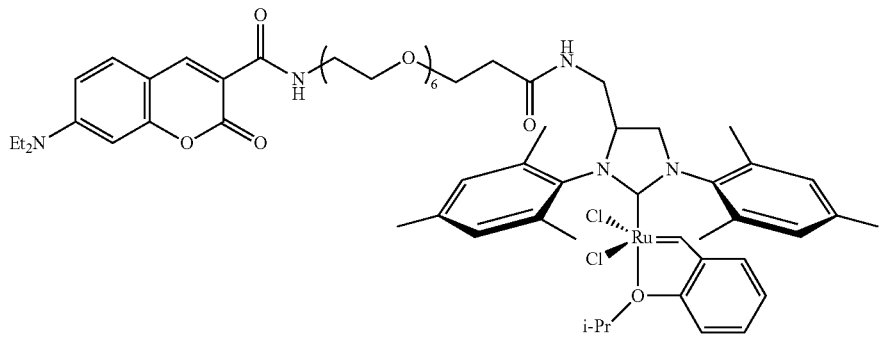

Ru6

2. Manufacture of Alb-Ru

The manufacture of alb-Ru was performed by reacting ruthenium catalysts Ru1-3, 6 and human serum albumin (HAS) to form alb-Ru complexes.

The composition of the reaction solution contained 30 μM human serum albumin (hereinafter HSA; 167 μL of 50 nmol, 300 μM stock solution (aqueous solution) used) and the catalyst (Ru1-3, 6) at various concentrations. The catalyst used was for example 37 μM of Ru1 (167 μL of 62 nmol, 370 μM stock solution (dioxane solution) used). The total reaction volume was filled to 1670 μL with PBS buffer (pH 7.4) comprising 10% dioxane. After starting the reaction by addition of HSA, the reaction mixture was gently mixed and incubated at 37° C. for 1 hour. Subsequently, with Amicon™ ultracentrifugation filter (30 kDa), the reaction solution was washed with PBS buffer and concentrated. Next, the concentrated alb-Ru solution was diluted with PBS buffer, and 1000 μL was obtained as 50 μM stock solution.

For confirmation of Alb-Ru complex formation, fluorescence assay that depends on the fact that coumarin-based molecules are sensitive to the polarity of the solvent was employed. Using Ru1-3, 6, the fluorescence intensity (measured value) obtained from 1:1 reaction of ligand-albumin is shown in FIG. 1.

As compared to the control (ligand only or HSA only), significantly high fluorescence level that is thought to be the indicator of alb-Ru complex formation was detected.

Moreover, in order to indirectly determine the Ru1-3, 6 binding site, HSA solution was preincubated together with 2 equivalents of either of the binding ligand (warfarin or ibuprofen) at 37° C. for 1 hour. Subsequently, the saturated binding curve of Ru1-3, 6 was generated with a mixture of albumin and binding ligand (FIG. 2).

Figure 2:
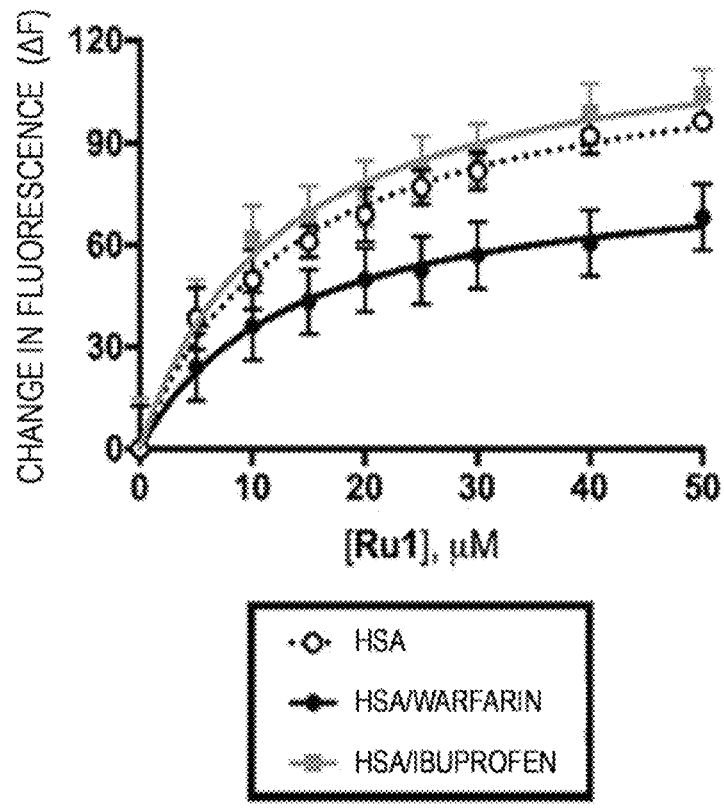
FIG. 2 show the saturated binding curves of performing reaction between HSA and warfarin or ibuprofen, and then reaction with ruthenium catalysts Ru1-3, 6.

From the results of FIG. 2, it became clear that the binding of Ru1-3, 6 was unaffected in the presence of ibuprofen, but significantly decreased in the presence of warfarin. This result strongly suggests that the drug binding site I of HSA is the main binding site of these compounds.

Example 2

Verification of Reactivity of Alb-Ru

Figure 3:
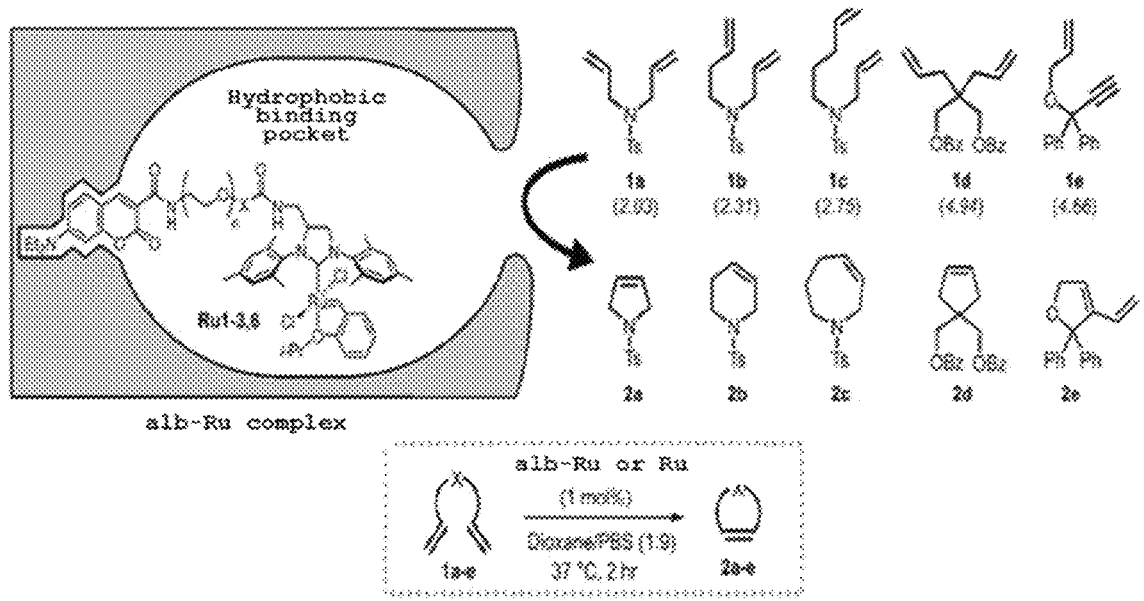
FIG. 3 shows the experimental system for testing the catalytic ability of alb-Ru complex employed in the Examples herein.

Next, the ability of the alb-Ru complex to catalyze ring-closing metathesis (RCM) of olefin 1a-1d and enyne 1e was examined (FIG. 3). Moreover, since alb-Ru1-3, 6 has differing PEG linker lengths, effective size and compatibility of the hydrophobic binding pocket was also verified.

The reaction solution essentially contained 1a-e as the substrate and the alb-Ru complex (i.e. Ru1-3, 6) in 1:9 dioxane:PBS buffer (pH 7.4). The reaction, after incubation at 37° C. for 2 hours, was quenched with dodecane thiol, further diluted with methanol, and the sample was filtered, subjected to HPLC analysis, and the metabolic turnover (TON) into respective products 2a-e was calculated. As control, a reaction using free ruthenium catalyst Ru1-3, 6 in solution (free-in-solution) was also carried out under similar conditions.

TABLE 1

| | | | Catalyst Linker Length | | | | |
| | | | Ru1 (n = 1) | | Ru2 (n = 2) | Ru3 (n = 3) | Ru6 (n = 6) |
| Entry | Sub | Catalyst | TON | r | TON | TON | TON |
| --- | --- | --- | --- | --- | --- | --- | --- |
| 1 | 1a | alb-Ru | 0.9 ± 0.01 | 0.35 | 0.3 ± 0.01 | 0.1 ± 0.01 | 0.2 ± 0.01 |
| 2 | | Ru | 2.6 ± 0.05 | | 1.5 ± 0.04 | 1.3 ± 0.01 | 0.8 ± 0.10 |
| 3 | 1b | alb-Ru | 2.3 ± 0.06 | 0.34 | 0.6 ± 0.01 | 0.3 ± 0.01 | 0.5 ± 0.01 |
| 4 | | Ru | 6.9 ± 0.01 | | 6.3 ± 0.02 | 5.2 ± 0.01 | 5.5 ± 0.03 |
| 5 | 1c | alb-Ru | 0.4 ± 0.19 | 0.25 | 0.2 ± 0.02 | 0.1 ± 0.01 | 0.1 ± 0.01 |
| 6 | | Ru | 1.6 ± 0.02 | | 1.9 ± 0.02 | 1.5 ± 0.10 | 1.8 ± 0.36 |
| 7 | 1d | alb-Ru | 19.7 ± 0.17 | 0.59 | 2.8 ± 0.04 | 0.9 ± 0.01 | 0.5 ± 0.03 |
| 8 | | Ru | 33.2 ± 0.18 | | 28.8 ± 3.77 | 28.8 ± 0.17 | 34.7 ± 0.18 |
| 9 | 1e | alb-Ru | 29.9 ± 0.20 | 0.57 | 1.2 ± 0.05 | 1.3 ± 0.01 | 0.6 ± 0.03 |
| 10 | | Ru | 52.5 ± 0.10 | | 55.7 ± 0.34 | 58.6 ± 0.10 | 41.5 ± 0.19 |

One of the first observations in this experiment was the correlation between the increase in the length of the PEG linker (between coumarin anchor and ruthenium catalyst) and the decrease in activity. For example, the metabolic turnover of the substrate 4,4-bis((benzoyloxy)methyl)-1,6-heptadiene 1d (Entry 7) was the highest in the presence of alb-Ru1 (19.7), abruptly declined in the presence of alb-Ru2 (2.8), and showed minuscule levels in the presence of alb-Ru6 (0.5). Given that the metabolic turnover (TON) obtained using free ruthenium catalyst Ru1 in solution generally remains within the range of 28-35 for all of the linker lengths employed (Entry 8), this observation result suggests that the hydrophobic binding pocket cannot accommodate a coumarin anchor-catalyst complex having a long linker.

Example 3

Verification of Biocompatibility of Alb-Ru

After confirming that the alb-Ru complex shows activity to catalyze ring-closing metathesis and enyne cross metathesis, we then aimed for verification of biocompatibility by evaluating the action of glutathione. Compound 1d was selected as the model substrate for this research.

One of the important experiments in this research was to examine the catalyst protection ability of alb-Ru1 against glutathione. As shown below, 1 mol % alb-Ru1 was employed, and substrate 1d was reacted together with addition of various concentrations of GSH. Note that depending on the concentration of alb-Ru1, glutathione was added at equal equivalents.

[Chemical Formula 6]

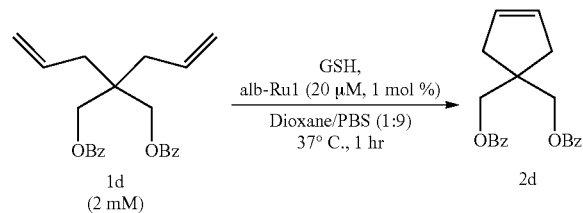

As a result, change in (calculated) TON was not observed up to 20 mM GSH (1000 equivalents of GSH against alb-Ru). Ultimately, with addition of 100 mM and 200 mM GSH, 60% and 82% decrease in TON compared to control was respectively recognized.

Figure 4:
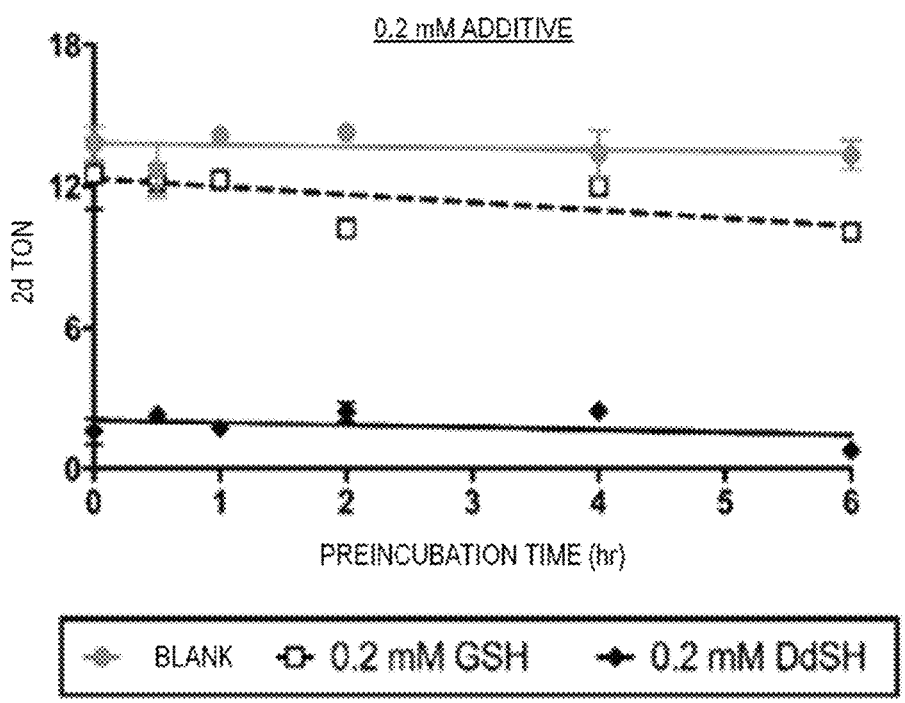
FIG. 4 shows the evaluation result of the catalytic ability of alb-Ru complex under a different condition.

In the next investigation, in order to learn the upper threshold limit of the GSH protection ability, the duration of the metal catalyst protection was evaluated. Specifically, alb-Ru1 was preincubated together with any of GSH, dodecane thiol, or PBS buffer (as blank) for various hours, then substrate 1d was added to the reaction solution, and the TON value was calculated after 1 hour of reaction. FIG. 4 shows the experiment of performing with physiologically appropriate GSH concentration (200 μM, 10 equivalents against alb-Ru1).

Figure 5:
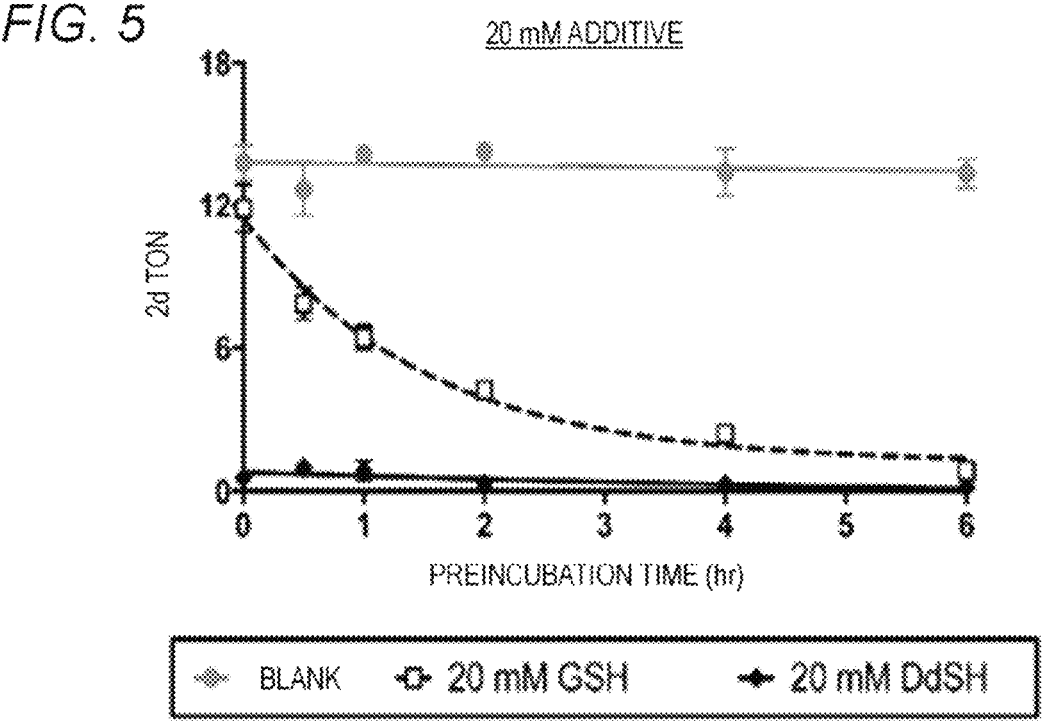
FIG. 5 shows the evaluation result of the catalytic ability of alb-Ru complex under a different condition.

The TON value measured after 6 hours of preincubation with GSH generally only showed slight decrease compared to the blank (PBS buffer). In contrast, in the experiment employing GSH at the upper threshold limit (20 mM, 1000 equivalents against alb-Ru1), a prominent (much larger) effect on reactivity was shown (FIG. 5).

In such a case, about 50% decrease in activity was observed after 1 hour of preincubation with GSH, whereas the activity nearly disappeared after 4 hours of preincubation.

In order to further evaluate the biocompatibility of Alb-Ru complex, substrate 1d was incubated with 10 mol % alb-Ru1 complex at 37° C. for 2 hours. The production yield of 2d was about 2% with 1:8:1 fetal bovine serum/DMEM medium/dioxane, and about 1% with 1:8:1 normal rat serum/PBS buffer/dioxane. However, since the collected starting material 1d was 8% and 3% respectively, the low production yield is likely to be attributable to the capture or degradation of the substrate by proteins that commonly exist in the serum.

Figure 6:
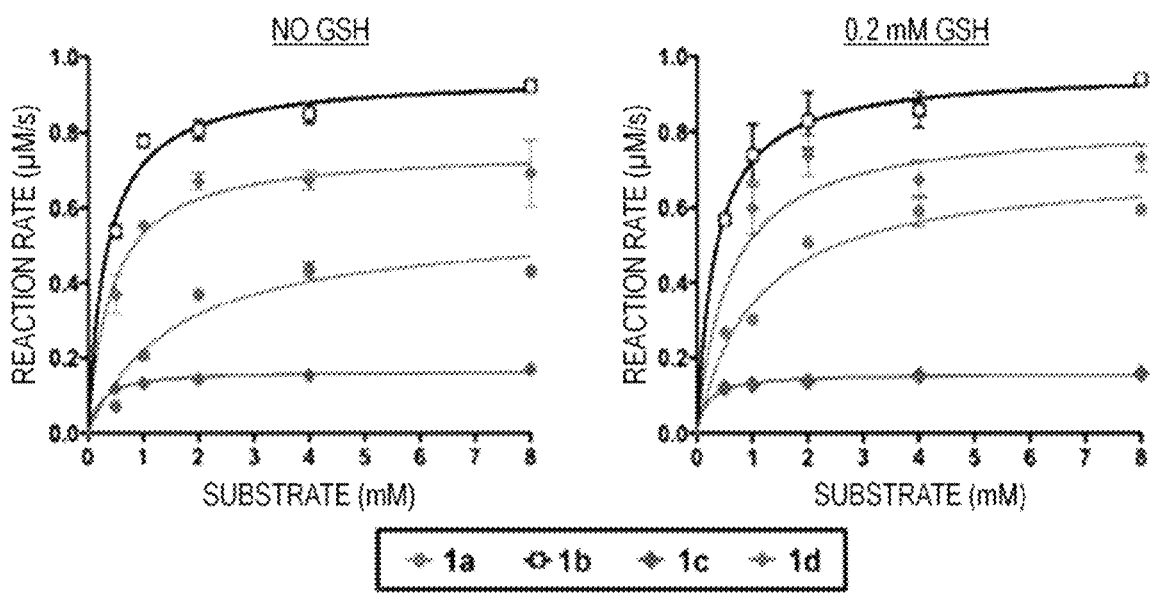
FIG. 6 shows the Michaelis-Menten kinetic parameters of substrates 1a-e in the presence or absence of GSH in regards to ArM activity (artificial metal enzyme activity).

In regards to ArM activity (artificial metal enzyme activity), Michaelis-Menten kinetic parameters of substrates 1a-e were calculated with or without addition of GSH (FIG. 6).

As a result, regardless of with or without GSH addition, there was only a slight change (within error) in kinetic numeric values measured for 1a-1e in ArM activity. Nonetheless, of particular importance is the difference in catalyst efficiency ($k_{cat}/K_M$) observed between these substrates. In particular, substrate 1e shows a $k_{cat}/K_M$ value of about $3\times10^3$ $M^{-1}s^{-1}$, and although this value compares poorly with the reactivity of a natural enzyme ($k_{cat}/K_M$ —$10^8$ $M^{-1}s^{-1}$), it is emphasized from this result that there is a possibility that the ArM of non-natural metal will reach reactivity equivalent to a natural enzyme.

Example 4

Mechanism of Glutathione Resistance

Figure 7:
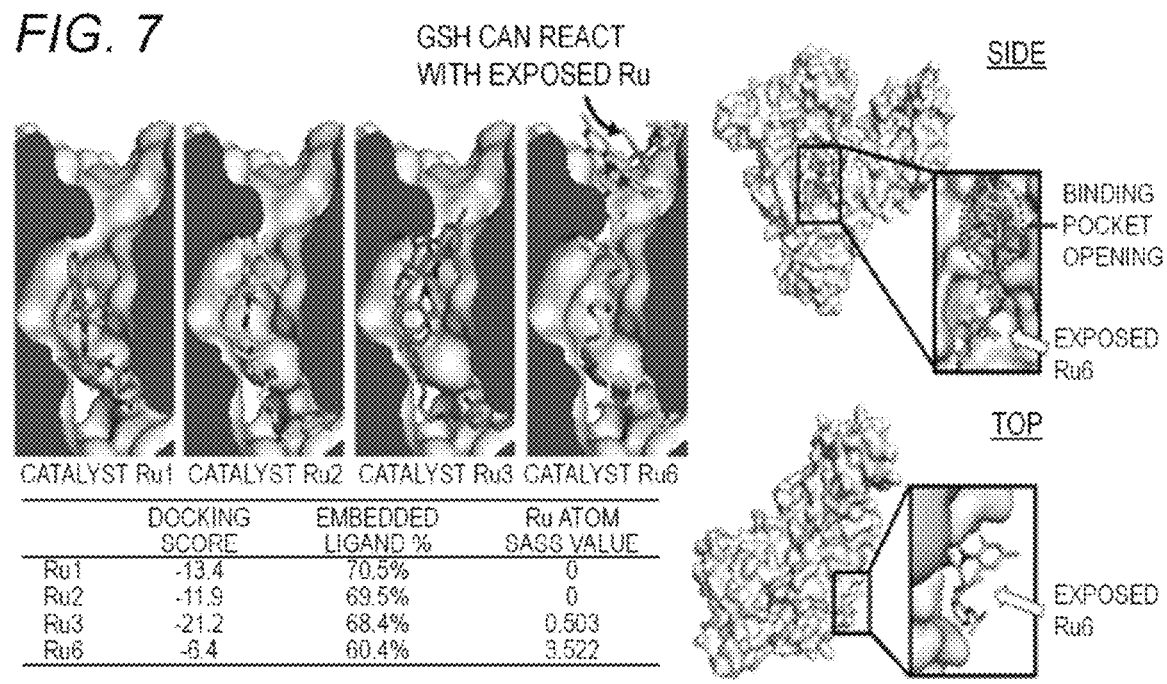
FIG. 7 shows the molecular modeling of when ruthenium catalysts Ru1-3, 6 are docked with human serum albumin (PDB:1H9Z).

In order to predict the extent of invasion and conformation in the hydrophobic binding pocket of the drug binding site I of albumin, Autodock 4.2 (Morris, G. M.; Huey, R.; Lindstrom, W.; Sanner, M. F.; Belew, R. K.; Goodsell, D. S.; Olson, A. J. J. Comput. Chem. 2009, 30, 2785-2791.) was employed in the GUI interface of AutoDockTools to research compound Ru1-3, 6 for molecular modeling that docks with human serum albumin (PDB:1H9Z). The result supports the fundamental assumption that the binding pocket of the drug binding site I of albumin is deep enough to accommodate the binding of a coumarin-ruthenium catalyst (e.g. Ru1) having a relatively short PEG linker length. However, as shown in FIG. 7, as the PEG linker length gradually gets longer (e.g. Ru6), the ruthenium portion gets pushed to the outside of the binding pocket, and its exposure to biomolecules in the solution is increased.

This theory was further supported by calculation of the relative solvent accessible surface area (SASA) of the ruthenium atom of the docking ligand, with the fact that the correlation with a longer PEG linker is increased. Note that in FIG. 7, zero value indicates atoms not exposed to the solvent.

Example 5

Targeting of Artificial Metal Enzyme

Another aspect to be considered for promoting the development of therapeutic ArM is the need for a targeting methodology to facilitate localization to particular organs/cells in the body.

If successful, application to prodrug therapy will be possible, which in turn is particularly beneficial for the development of medicinal candidates having risks of side effects, such as anti-cancer therapy based on cytotoxic molecules.

It has been found that since the complexity of glycocalyx that envelops the surface of different eucaryotic cells is changing, glycoalbumin bound to a particular combined N-glycan conglomerate can exert different recognition ability or binding between different cancer cells. In an essential research with the objective to test whether these glycoalbumins have the ability to act as in vivo supports, in regards to protein labeling based on propargylic ester, glycoalbumin comprising a gold catalyst was localized in a particular organ of a live mouse by the N-glycan structure thereof and showed in vivo catalytic activity (Tsubokura, K.; Vong, K. K. H.; Pradipta, A. R.; Ogura, A.; Urano, S.; Tahara, T.; Nozaki, S.; Onoe, H.; Nakao, Y.; Sibgatullina, R.; Kurbangalieva, A.; Watanabe, Y.; Tanaka, K. Angew. Chem. Int. Ed. Engl. 2017, 56, 3579-3584.).

In order to develop and investigate applicability to cancer, a uniform conglomerate of N-glycans at the sialic acid α(2,3)-linked terminal was selected as the target group. This selection was made based on a previous research which showed that glycoalbumin(2,3-Sia) having sialic acid α(2,3)-bond can preferentially accumulate in SW620 human colon adenocarcinoma cells, which also showed moderate binding to A549 human pulmonary alveolar basement epithelial adenocarcinoma cells and HeLa human cervical cancer-derived cells (Ogura, A.; Urano, S.; Tahara, T.; Nozaki, S.; Sibgatullina, R.; Vong, K.; Suzuki, T.; Dohmae, N.; Kurbangalieva, A.; Watanabe, Y.; Tanaka, K. ChemComm 2018, 54, 8693-8696.). This effect is likely caused by the overexpression of galectin-8 which is known as a well-known α(2,3)-linked sialic acid (Lahm, H.; Andre, S.; Hoeflich, A.; Fischer, J. R.; Sordat, B.; Kaltner, H.; Wolf, E.; Gabius, H.-J. J. Cancer Res. Clin. Oncol. 2001, 127, 375-386; Carlsson, S.; Oberg, C. T.; Carlsson, M. C.; Sundin, A.; Nilsson, U. J.; Smith, D.; Cummings, R. D.; Almkvist, J.; Karlsson, A.; Leffler, H. Glycobiology 2007, 17, 663-676.).

First, glycosylated ArM (GArM)-Ru1(2,3-Sia) having ruthenium catalyst Ru1 fixed thereon was prepared, and then the targeting ability towards SW620 human colon adenocarcinoma cells was evaluated in a binding experiment. In order to evaluate specific binding of GArM-Ru1(2,3-Sia) to cancer cells, cancer cells were seeded in a 96-well plate with a transparent bottom at a density of $10^4$ cells/well, and cultured overnight. Subsequently, the medium was removed, and [1] GArM-Ru1(2,3-Sia), [2] alb-Ru, [3] GA(2,3-Sia), or [4] Ru1 were added so that each will have a final concentration of 10 μM. After incubating the cells at 37° C. for 3 hours, the medium was removed, this was washed with PBS buffer (3 times), and fixed on the plate with formaldehyde reagent. Cell observation was performed with BZ-X710 All-in-one Fluorescence Microscope™ from Keyence, and fluorescent images and bright field images were recorded. ET-EBFP2/Coumarin/Attenuated DAPI Filter Set Cat #49021 (Chroma Technology Corp., Vermont, USA) was employed for detection of coumarin-derived fluorescence. Imaging images were taken at 20× magnification, and analyzed with BZ-X Analyzer (from Keyence) software.

Figure 8:
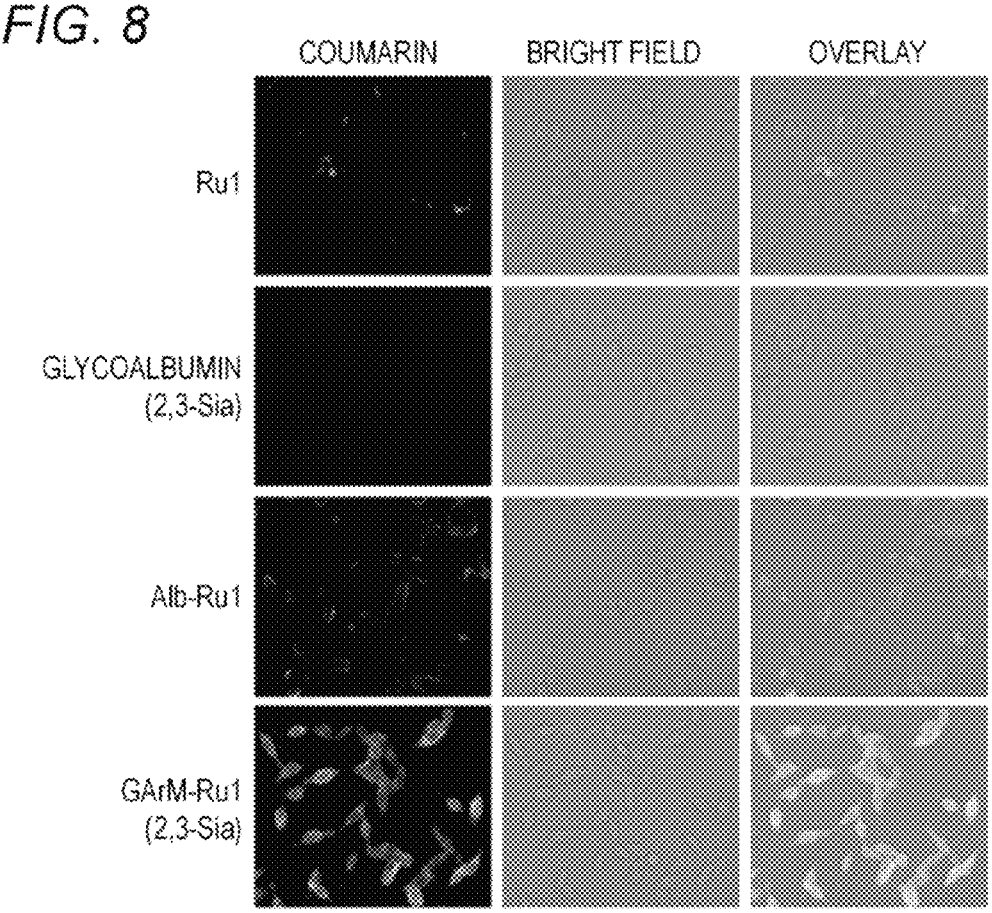
FIG. 8 is cell imaging results showing that GArM-Ru1 (2,3-Sia) is better accumulated in SW620 human colon adenocarcinoma cells.

The result is shown in FIG. 8. By cell imaging utilizing the fluorescent luminescence of coumarin bound to HSA, a more intense fluorescence accumulation was recognized in SW620 human colon adenocarcinoma cells incubated with GArM-Ru1(2,3-Sia) compared to its control.

Figure 9:
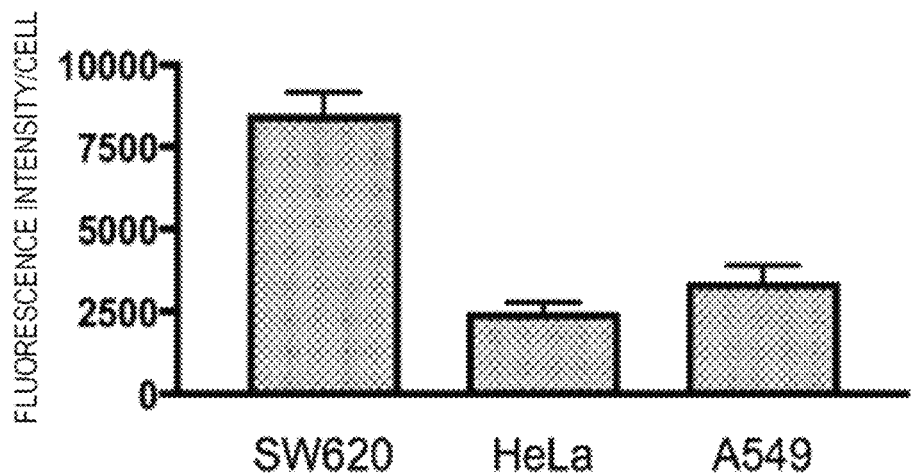
FIG. 9 shows the comparison between SW620 human colon adenocarcinoma cells, HeLa human cervical cancer-derived cells, and A549 human pulmonary alveolar basement epithelial adenocarcinoma cells in regards to accumulation of GArM-Ru1(2,3-Sia).

As an additional test, a similar experiment was also performed with HeLa human cervical cancer-derived cells and A549 human pulmonary alveolar basement epithelial adenocarcinoma cells. Consistent with previous reports, it was observed that accumulation of GArM-Ru1(2,3-Sia) in SW620 human colon adenocarcinoma cells was higher than that in HeLa human cervical cancer-derived cells and A549 human pulmonary alveolar basement epithelial adenocarcinoma cells (FIG. 9).

Example 6

Prodrug Therapy

Next, applicability of GArM-Ru complex targeting anticancer therapy was investigated. Umbelliprenin (2h) was selected as the initial investigation of drug candidates that are activated by ring-closing metathesis.

[Chemical Formula 7]

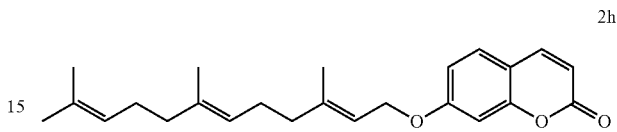

2h

Umbelliprenin which is known as a natural product extracted from Ferula plants has shown cytotoxic activity against various cancer cell strains (Shakeri, A.; Iranshahy, M.; Iranshahi, M. J. Asian. Nat. Prod. Res. 2014, 16, 884-889; Rashidi, M.; Khalilnezhad, A.; Amani, D.; Jamshidi, H.; Muhammadnejad, A.; Bazi, A.; Ziai, S. A. J. Cell. Physiol. 2018, 233, 8908-8918; Jun, M.; Bacay, A. F.; Moyer, J.; Webb, A.; Carrico-Moniz, D. Bioorganic Med. Chem. Lett. 2014, 24, 4654-4658). The mechanism of the cytotoxicity is shown to be induction of apoptosis by arresting of the cell in G1 phase, further activation of caspase-8 and 9, and down regulation of Bcl-2 and Mcl-1 (Barthomeuf, C.; Lim, S.; Iranshahi, M.; Chollet, P. Phytomedicine 2008, 15, 103-111; Gholami, O.; Jeddi-Tehrani, M.; Iranshahi, M.; Zarnani, A. H.; Ziai, S. A. Iran J. Pharm. Res. 2013, 12, 371-376; Gholami, O.; Jeddi-Tehrani, M.; Iranshahi, M.; Zarnani, A. H.; Ziai, S. A. Iran J. Pharm. Res. 2014, 13, 1387-1392). Due to its very high hydrophobicity (mainly rendered by the farnesyl portion), umbelliprenin prodrug (1h) was theorized to be an ideal substrate for albumin-based ArM.

[Chemical Formula 8]

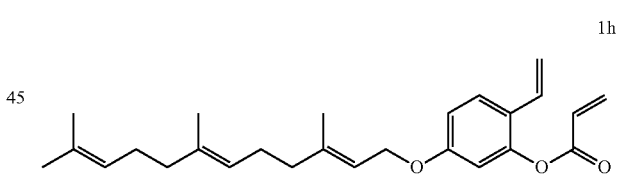

1h

Figure 10:
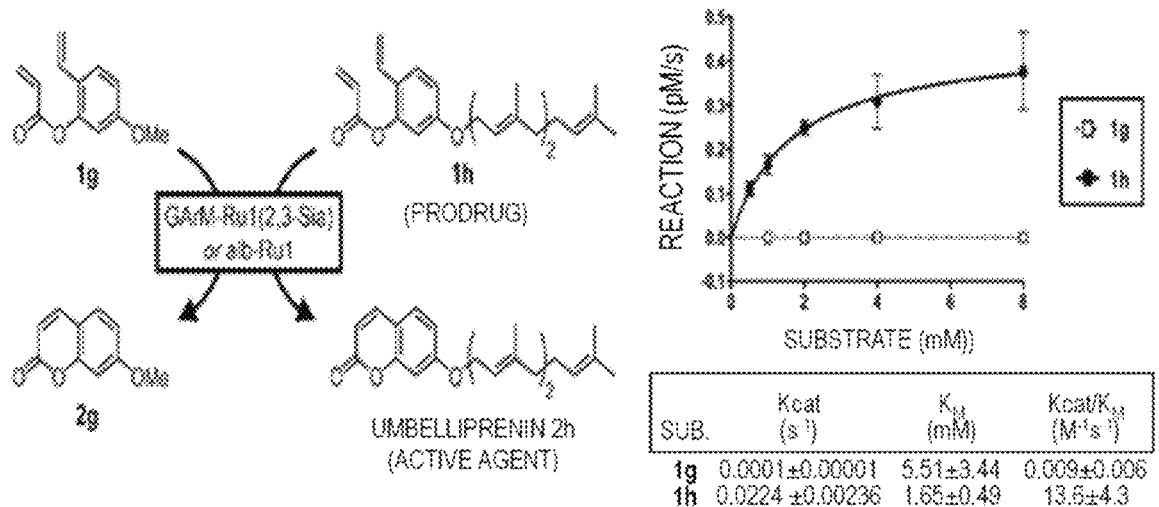
FIG. 10 shows a kinetic experiment in regards to the activation of prodrugs 1g and 1h by GArM-Ru complex.

In order to verify this, simplified coumarin derivative 1g and umbelliprenin prodrug 1h were both employed for kinetic experiment (FIG. 10).

Although coumarin precursors are ordinarily known to have poor RCM reactivity under aqueous conditions, a very slight reactivity ($k_{cat}/K_M<1$) of coumarin derivative 1g was unexpected. An explanation for this is shown by a binding experiment result that precursor 1g has very low binding affinity ($K_D$ of about 129 μM) against albumin. On the other hand, the significantly high activity (at least 1500-folds higher $k_{cat}/K_M$ compared to 1g) of hydrophobic prodrug 1h is likely attributed to the long alkyl chain portion of 1H that facilitates the entry into the hydrophobic binding pocket.

Next, a series of experiments were performed in order to evaluate the in cellulo activity of the anticancer approach based on GArM.

Cytotoxicity test was performed by using prodrug 1h at set particular concentrations (32 μM for SW620 human colon adenocarcinoma cells; 64 μM for HeLa human cervical cancer-derived cells and A549 human pulmonary alveolar basement epithelial adenocarcinoma cells) and changing the amount of GArM-Ru1 added.

Cell survival rate measurement was performed with Cell-Titer 96™ Aqueous One Solution Cell Proliferation Assay (MTS) from Promega. Cultured cells were seeded in a Falcon™ 96-well microplate at a density of about $10^3$ cells/well, and cultured overnight. Subsequently, the medium was removed, the compounds at various concentrations were added. DMSO was used for dissolving the compounds, and the DMSO concentration was 1% for addition to the cells. After incubating for 96 hours, the cell culture medium was substituted with 85 μL of fresh medium. Subsequently, 15 μL of MTS reagent was added, this was incubated at 37° C. for 2.5 hours, and then absorbance was measured at 490 nm. The absorbance of cells with addition of 1% DMSO as the control was set at 100%, and the cell survival rate was calculated.

Figure 11:
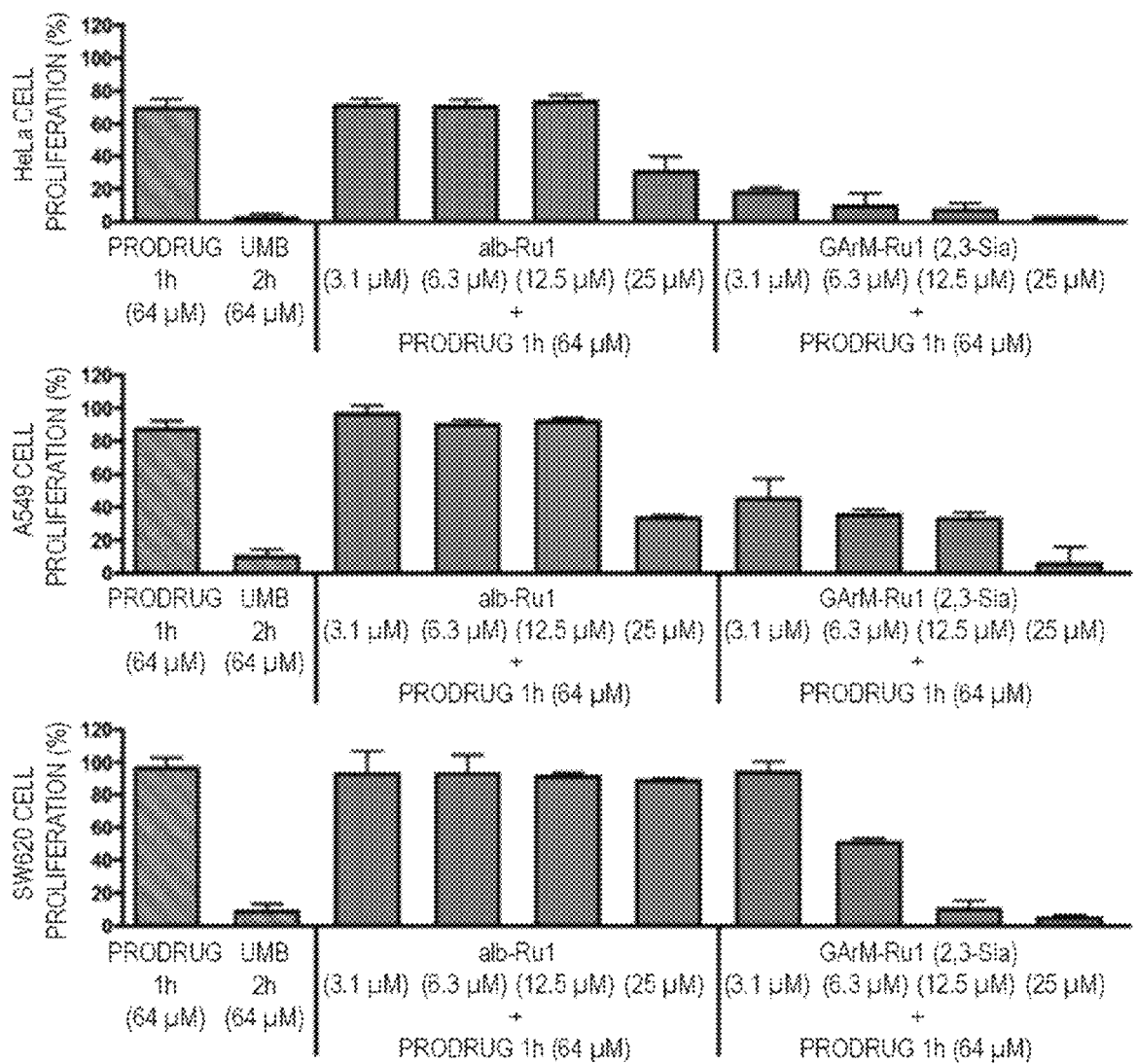
FIG. 11 shows the comparison of cell growth inhibition effect on cancer cell strains by prodrug, prodrug and alb-Ru1, or prodrug and GArM-Ru1.

In order to explain the targeting effect by sugar chains, experiments under similar conditions were performed with alb-Ru1 without sugar chain as the control. From these results, in all three cancer cell strains, the mixture of prodrug 1h and GArM-Ru1 significantly decreased cell proliferation (<5%), and the effect surpassed the effect at corresponding concentrations of prodrug 1h and GArM-Ru1 (FIG. 11). Another important observation was that the cytotoxic activity of the mixture of prodrug 1h and alb-Ru1 was far lower in effectiveness. This suggests that targeting by sugar chains is essential for localization of metal catalyst to the cell surface or inside cells.

Example 7

Synthesis of Artificial Metalloenzyme (ArM) that Detects Ethylene (ArM Ethylene Probe; AEP)

Figure 12:
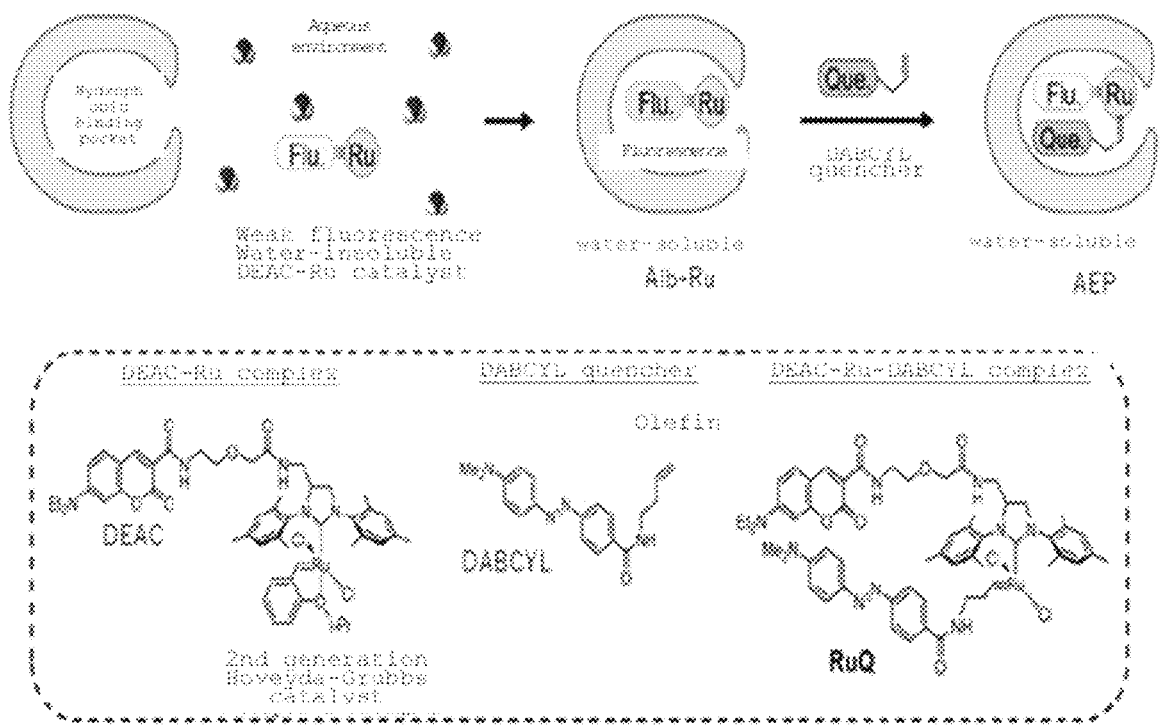
FIG. 12 shows the synthetic scheme of the ArM ethylene probe (AEP).

FIG. 12 describes the synthetic scheme of ArM ethylene probe (AEP).

Fluorescence emitted by 7-diethylamino coumarin (DEAC) per se has high sensitivity to the polarity of the surrounding solvent, and the quantum yield of DEAC-Ru increases to about 20-folds by the change from being under a polar environment (10% dioxane/water) to a nonpolar environment (60% dioxane/water). Accordingly, in this synthesis, AEP was synthesized based on the reaction between DABCYL inactivating agent comprising olefin (quencher) and alb-Ru.

7-1. Preparation of AEP

Thirty micromolar HSA solution (167 μL from 50 nmol, 300 μM aqueous solution) and 37 μM DEAC-Ru solution (167 μL from 62 nmol, 370 μM dioxane solution) were mixed to prepare alb-Ru. The reaction solution was filled to a total amount of 1670 μL with pH 7.4 PBS buffer solution comprising 10% dioxane. After starting the reaction by addition of HSA, the reaction solution was gently stirred and incubated at 37 degrees for 1 hour. Subsequently, the reaction solution was concentrated with Amicon Ultra Centrifugal filter (30 kDa), and washed three times with PBS buffer solution.

Water was added to the concentrated alb-Ru solution to dilute to 50 μL, and 1 mM stock solution was obtained. In order to prepare AEP solution, a mixed solution of 100 μM alb-Ru solution (50 μL from 50 nmol, 1 μM aqueous solution) and 500 μM DABCYL quencher solution (450 μL from 250 nmol, 555 μM DMSO:water=1:8 solution) was made. The reaction solution was gently stirred and incubated at 37 degrees for 5 minutes. Subsequently, the reaction solution was concentrated with Amicon Ultra Centrifugal filter (30 kDa), and washed three times with PBS buffer solution. Water was added to the concentrated AEP solution to dilute to 500 μL, and 100 μM stock solution was obtained.

The fluorescence intensity of the protein complex (alb-Ru, AEP) was measured with JASCO FP-6500 Spectrofluorometer equipped with JASCO FMP-963 microplate reader. In order to prepare samples, both alb-Ru and AEP were prepared into aqueous solutions at a concentration of 10 μM. The samples were then aliquoted (100 μL) into a 96-well microplate and measured at $\lambda_{EX}$=420 nm/$\lambda_{EM}$=463 nm. All measurements were performed three times.

Moreover, circular dichroism (CD) analysis was performed in order to distinguish the major change in the structure of the protein complex (alb-Ru, AEP) employed in this research. For CD spectrum, 0.1 cm cells were used, and J-1500 Circular Dichroism Spectrometer (JASCO) was employed for measurement. A 10% dioxane aqueous solution was used as the blank, and this was automatically subtracted from the sample during scan. Data was recorded for 200-250 nm at a scan speed of 100 nm/min. The concentration of each protein complex was retained at 2.3 μM.

[Result]

Figure 13:
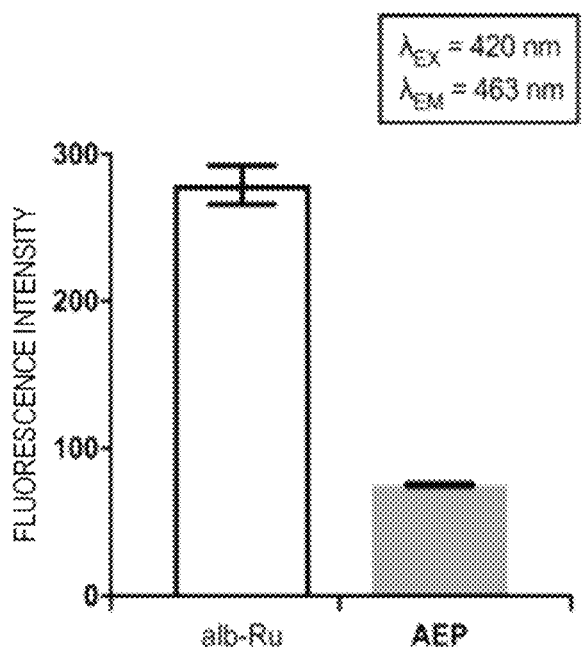
FIG. 13 shows the observed fluorescence intensity of alb-Ru compound compared to the AEP probe.
Figure 14:
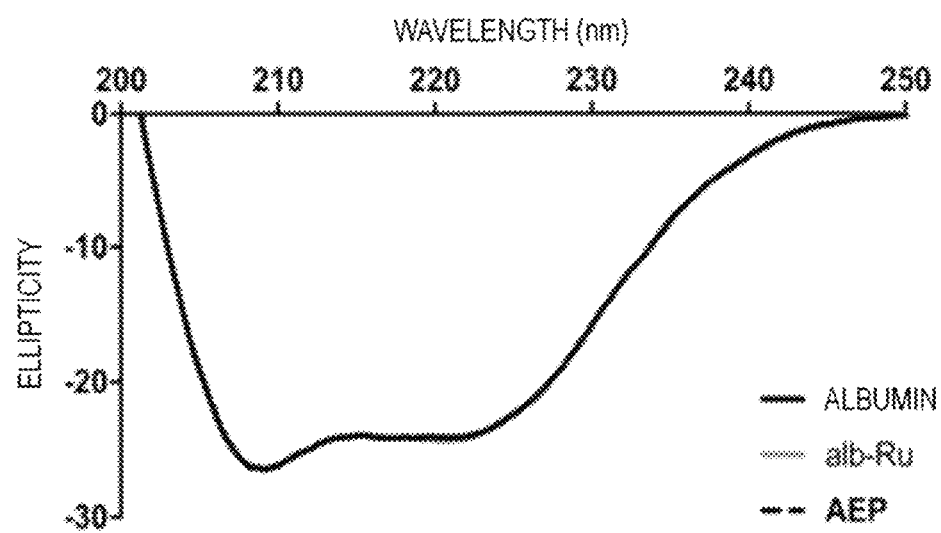
FIG. 14 shows the comparison of CD spectra for examining the change in the folding structure of various protein compounds in this research.

The RuQ complex (DEAC-Ru-DABCYL complex) present in the binding pocket of albumin had a significantly low fluorescence intensity due to the quencher, and this is also clear from comparing the fluorescence intensity of alb-Ru and AEP probe in FIG. 13. Further, since the circular dichroism (CD) of these completely overlapped, it was confirmed that no major structure degeneration in the protein was seen (FIG. 14).

7-2. Detection of Ethylene by AEP

The ethylene detection mechanism by AEP is by reacting ethylene with the ruthenium catalyst in AEP to allow substitution with the DABCYL quencher and activation of the fluorescence signal. Accordingly, in this Example, AEP was employed for detection of ethylene in fruits and plants.

[Imaging of Kiwi Fruit]

Immature or mature kiwi fruits were purchased at a grocery store. In order to obtain fragments comprising the outer pericarp, loculus, and columella, kiwi fruits were cut into about 2.0 cm×4.5 cm sizes with a kitchen knife to prepare kiwi fruit fragments. In order to track ethylene production, 170 μL of AEP (400 μM solution) was poured in the center of a 10-cm dish. Subsequently, the samples were allowed to act on the AEP solution. The samples were incubated at room temperature, and imaging was performed after a certain amount of time (after 1, 24 hours). Keyence BZ-X710 All-in-one Fluorescence Microscope™ equipped with ET-EBFP2/Coumarin/Attenuated DAPI Filter Set Cat #49021 (Chroma Technology Corp.) was employed for imaging. Bright field image (color) and the fluorescent image were obtained at exposure settings of 1/25 seconds and 1/3.5 seconds, respectively. Multiple imaging images were obtained at 4× magnification, image binding and analysis was performed with BZ-X Analyzer software (Keyence).
[Imaging of *Arabidopsis thaliana*]

*Arabidopsis thaliana* was grown in soil at 23 degrees with light intensity of 85 μmol m$^{-2}$s$^{-1}$. Photoperiodicity of 10 hours of light and 14 hours of dark was applied. In order to track ethylene production, leaves were first taken from 4 to 6-week plants. Subsequently, the transparent epidermal skin was peeled from the leaf with a clamp, and placed in a 96-well plate with a transparent bottom. After adding water (100 μL), samples were incubated at room temperature for 12 hours in order to eliminate the effect of damage stress. Depending on the experiment condition, various solutions such as 1 mM ACC solution (2 μL of 55 mM aqueous solution), 4.8 μM flg22, or elf18 solution (5 μM, 100 μM aqueous solution), and OD$_{600}$=0.02 *Pseudomonas* bacteria solution (2 μL of OD$_{600}$=1.0 standard solution) were added as necessary. In an experiment comprising ACC and *Pseudomonas* bacteria, 12 hours of incubation at room temperature was applied. On the other hand, in an experiment comprising PAMP, 6 hours of incubation at room temperature was applied. Subsequently, these solutions were completely removed from epidermal skin samples, and 100 μM AEP solution (50 μL from stock solution) was added. After 30 minutes, the solution was completely removed and washed with water, and then imaging was performed with Keyence BZ-X710 All-in-one Fluorescence Microscope™ equipped with ET-EBFP2/Coumarin/Attenuated DAPI Filter Set Cat #49021 (Chroma Technology Corp.). Imaging images were obtained at 20×, 40× magnification, and the bright field image (monochrome) and the fluorescent image was obtained at exposure settings of 1/400 seconds and 1/30 seconds, respectively. Multiple imaging images were obtained at 4× magnification, and analysis was performed with BZ-X Analyzer software (Keyence).

[Result]
Spatial Detection of Ethylene in Fruits

Figure 15:
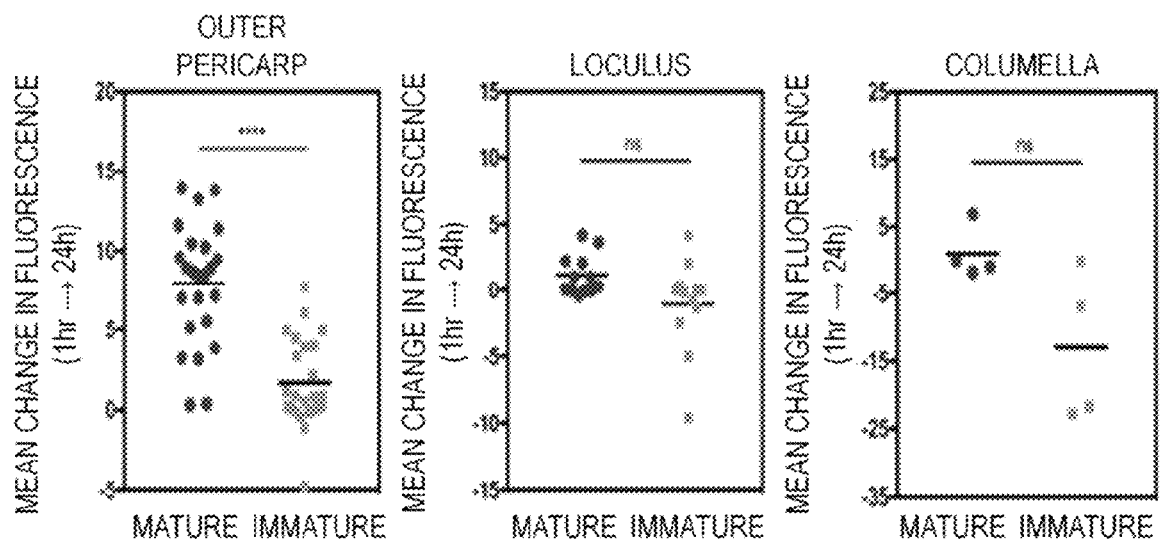
FIG. 15 shows the result of observing the change in the amount of ethylene produced expressed in various organelles (the outer pericarp, loculus, and columella) in different developmental stages (immature and mature) of kiwi fruits with AEP. The number of samples is the outer pericarp (n=24), loculus (n=2), and columella (n=4), and statistical analysis was performed with a t-test of a pair of samples. *P<0.03, P<0.002, *P<0.0002, ****P<0.0001, ns=not essential.

In general, in climacteric fruits, production of autocatalytic ethylene (system 2) progresses during the process of maturing. This is similar for external stimulation such as damage stress or pathogen infection. In this research, endogenous ethylene was first examined by an AEP probe. In kiwi fruits, it is reported that during maturing, the amount of ethylene produced is increased in the outer pericarp via upregulation of the ACS isogene. In an imaging experiment of kiwi fruit with AEP, focus was placed on observing the change in the amount of ethylene production expressed in various organelles (the outer pericarp, loculus, and columella) in different developmental stages (immature and mature). As summarized in FIG. 15, as the fruit matures from the immature state, significant increase in fluorescence intensity was observed in the outer pericarp. On the other hand, the change in fluorescence intensity in the loculus and columella of kiwi fruit was not observed so much. From these results, it became clear that the use of AEP is a promising means for detecting ethylene expression during mature and maturing period of fruits.

Ethylene Detection in Plants

In order to investigate the effect of AEP detection in plants, a small flowering plant *Arabidopsis thaliana* (Brassicaceae family) was selected as the model plant. In order to show with certainty that it is possible to detect the production of ethylene by APE, a comparison experiment was performed with a low-molecular known to control ethylene production and various plant variants involved in ethylene production.

In this research, *Arabidopsis thaliana* Col-0 ecotype was used as the wild-type model plant. Further, a wide range of various plant variants such as acs1/2/6/4/5/9/7/11 or eto1-1 were also used. Variant acs1/2/6/4/5/9/7/11 is a variant with 8 ACS genes knocked out, and the ethylene amount does not increase even when a pathogen invades. This is because ACS is responsible for an important role related to the biosynthetic pathway of ethylene. Further, eto1-1 which excessively produces ethylene was employed as another variant. Proteasome-dependent degradation is suppressed through the expression of ethylene-overexpression protein 1 (ETO1), and ACS activity is positively controlled. This is based on interaction between the C-terminal of type II ACS and ETO1.

Figure 16:
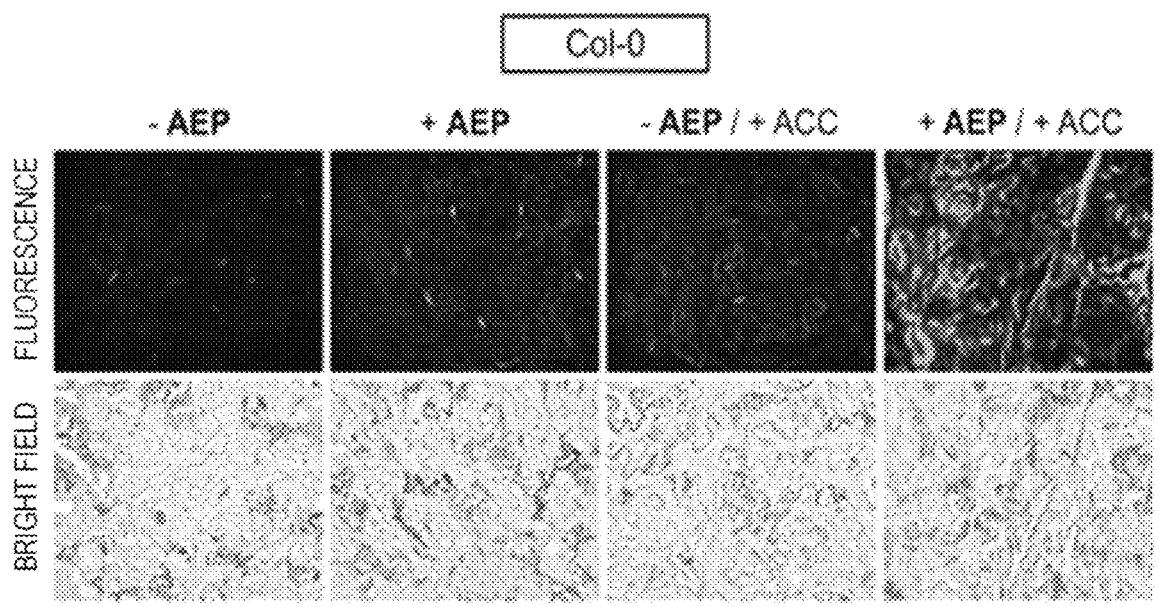
FIG. 16 shows the fluorescence intensity and bright field microscope imaging images (40× magnification) of the epidermis of wild-type Col-0 (b) that was applied AEP (100 µM), as well as the results of further addition of an ethylene biosynthesis accelerator ACC (1 mM) and detection.
Figure 17:
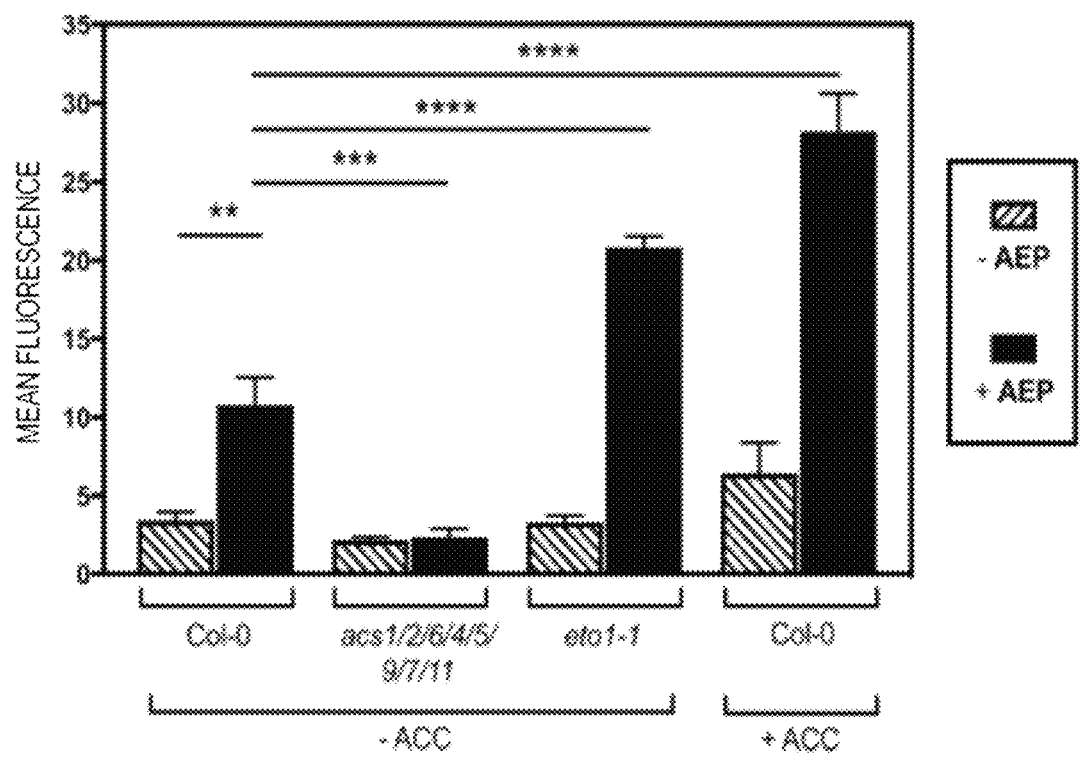
FIG. 17 shows the result of observing the amount of ethylene produced from *Arabidopsis thaliana* by addition of ACC with fluorescence intensity. All values were obtained in triplicate experiments. Statistical analysis was performed with one-way analysis of variance of Tukey's multiple comparison test. *P<0.03, P<0.002, *P<0.0002, ****P<0.0001, ns=not essential.

Imaging images of Col-0 incubated at room temperature with or without addition of AEP are shown in FIG. 16. As quantified in FIG. 17, significant increase in fluorescence intensity was observed, thereby confirming that AEP can be utilized for ethylene detection in the epidermal skin of *Arabidopsis thaliana*. As positive control, comparison was made with (an ethylene product of) Col-0 externally stimulated by ACC. As anticipated, a higher increase in fluorescence intensity was shown compared to wild-type Col-0.

Example 8

Selective Tagging of cRGD Against Cancer Cells by Glycosylated ArM

It has been reported in many researches that cyclic Arg-Gly-Asp (cRGD) pentapeptide inhibits αv$\beta_3$ and αv$\beta_5$ integrins overexpressed on the cancer cell surface, and is effective for preventing adherence to the extracellular matrix (J. S. Desgrosellier, D. A. Cheresh, Integrins in cancer: Biological implications and therapeutic opportunities. Nat. Rev. Cancer 10, 9-22 (2010).; M. Pfaff, K. Tangemann, B. Muller, M. Gurrath, G. Muller, H. Kessler, R. Timpl, J. Engel, Selective recognition of cyclic RGD peptides of NMR defined conformation by αIIbβ3, αvβ3, and α5β1 integrins. J. Biol. Chem. 269, 20233-20238 (1994).; and M. Aumailley, M. Gurrath, G. Muller, J. Calvete, R. Timpl, H. Kessler, Arg-Gly-655 Asp constrained within cyclic pentapeptides. Strong and selective inhibitors of 656 cell adhesion to vitronectin and laminin fragment P1. FEBS Lett. 291, 50-54 657 (1991).). Moreover, it has been shown that an RGD-based antagonist against integrins expressed on vascular endothelial cells facilitates tumor by inhibiting neovascularization (P. C. Brooks, A. M. P. Montgomery, M. Rosenfeld, R. A. Reisfeld, T. Hu, G. Klier, D. A. Cheresh, Integrin αvβ3 antagonists promote tumor regression by inducing apoptosis of angiogenic blood vessels. Cell 79, 1157-1164 (1994).; and D. G. Stupack, D. A. Cheresh, Integrins and angiogenesis. Curr. Top. Dev. Biol. 64, 207-238 (2004).).

In this Example, it was investigated whether glycosylated ArM (GArM) may be used for selective cell tagging (SeCT) therapy for destroying adherence of cancer cells at single cell level, which mimics the seeding process of micrometastasis. Specifically, it was verified whether this is possible by selectively accumulating GArM complex targeting HeLa to cancer cells, and then selectively tagging cRGD to surface proteins.

8-1. Preparation of cRGD-PE
The scheme employed for preparation of cRGD-PE was as follows:
[Chemical Formula 9]
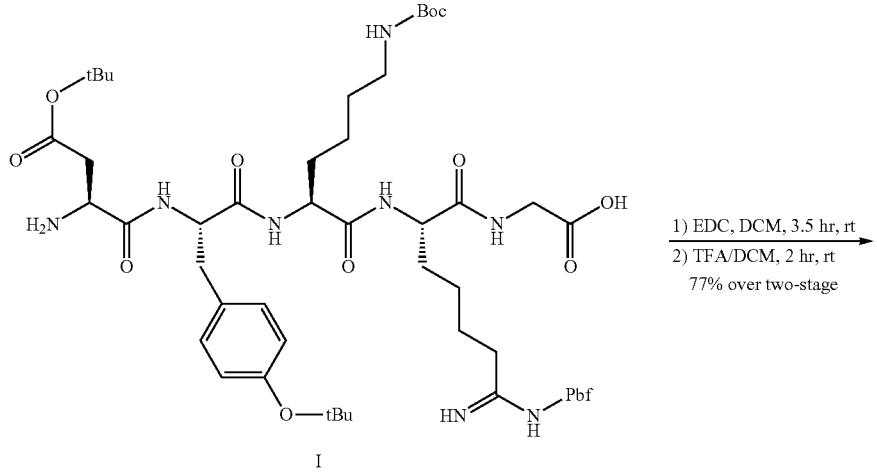
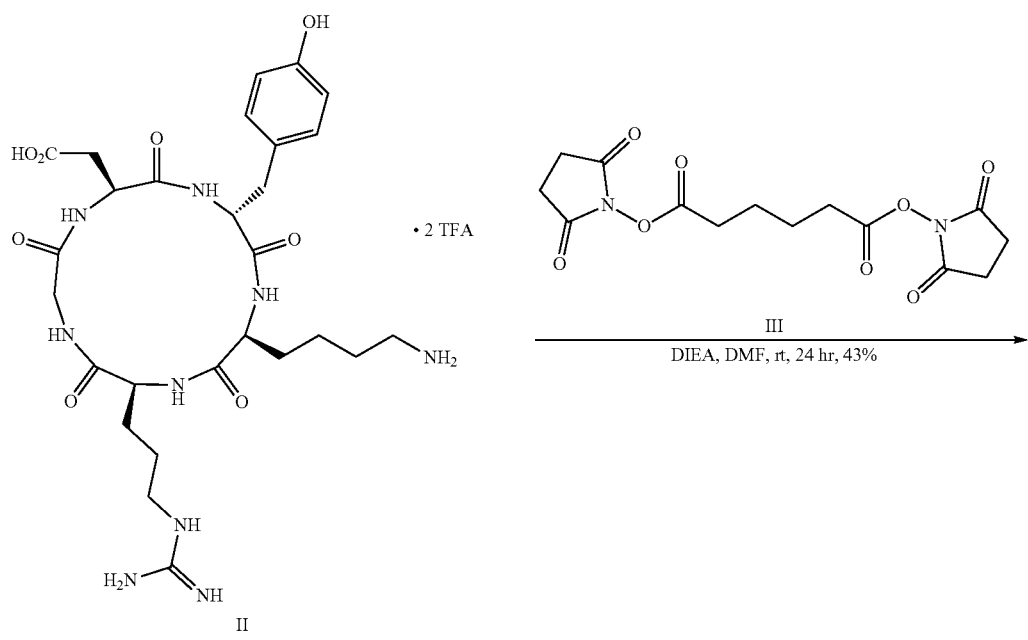

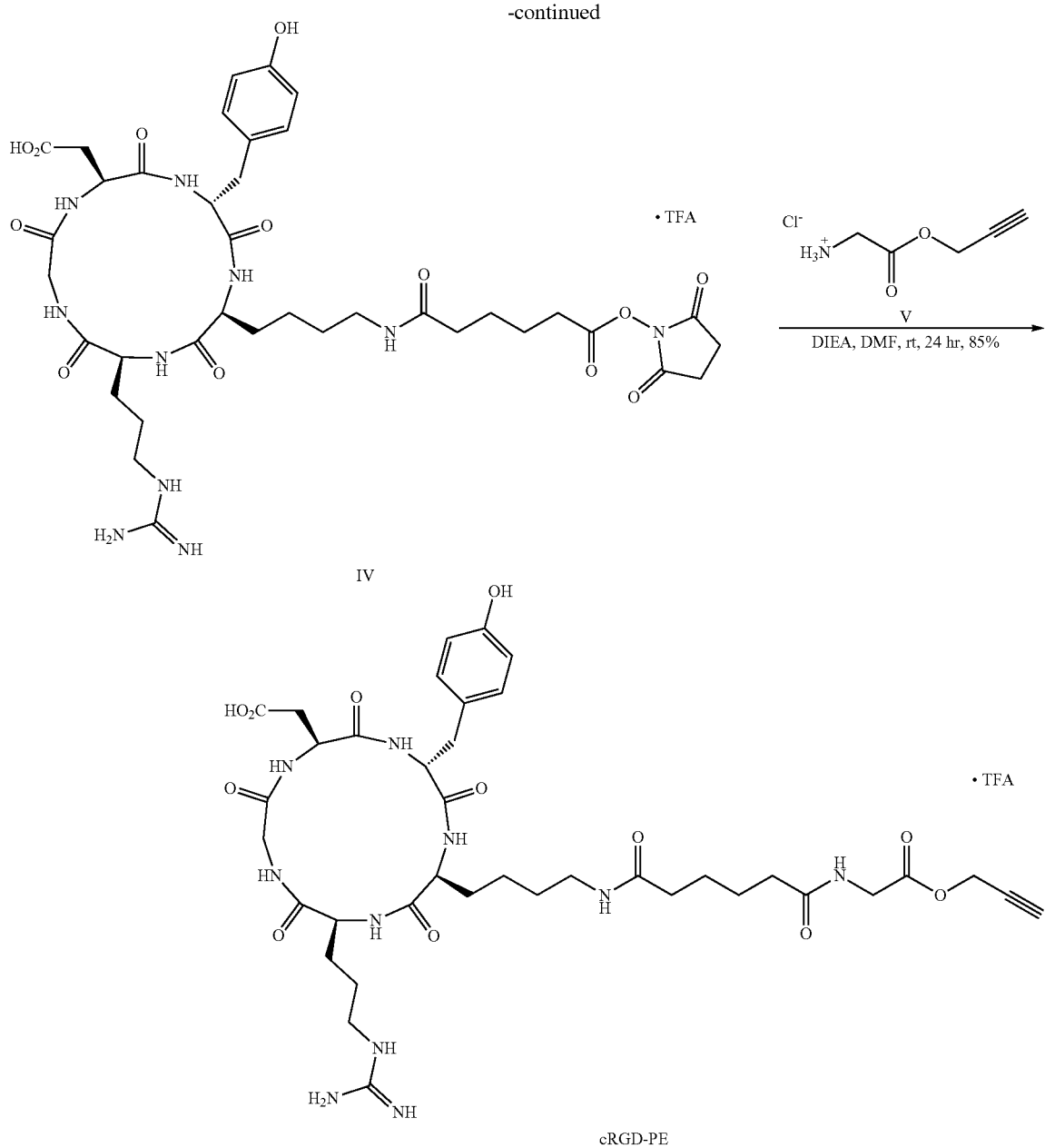

cRGD-PE (Preparation of Compound I)

Synthesis was performed by a standard solid phase peptide synthesis method. After cutting out from the solid phase support, the mixture was directly purified by a reverse phase HPLC with a linear gradient condition of 20-80% acetonitrile aqueous solution (0.1% TFA) over 40 minutes. Yield: 2.92 g, 89%, ESI-HRMS m/z calcd for $C_{53}H_{83}N_9O_{14}S$ ([M+H]$^+$) 1102.5853, found 1102.5859.

(Preparation of Compound II)

Compound I (90.1 mg, 0.0833 mmol) and EDC (17.6 mg, 0.0916 mmol) were dissolved in methylene chloride (0.5 mL). Subsequently, the solution was stirred at room temperature for 3.5 hours. For workup, methylene chloride was added, the organic layer was washed with water/saturated saline, dried with magnesium sulfide, and concentrated under reduced pressure. Production of the target substance was confirmed by mass spectrometry of the residue obtained. ESI-HRMS m/z calcd for $C_{53}H_{81}N_9O_{13}S$ ([M+H]$^+$) 1084.5747, found 1084.5744.

Subsequently, this protected peptide obtained was dissolved in a solution of TFA/methylene chloride (1:1) for 2 hours to perform deprotection. The mixture was concentrated under reduced pressure, and directly purified by a reverse phase HPLC with a linear gradient condition of 20-80% acetonitrile aqueous solution (0.1% TFA) over 40 minutes. Yield: 54.5 mg, 77% (2-step yield). ESI-HRMS m/z calcd for $C_{27}H_{41}N_9O_8$ ([M+H]$^+$) 620.3151, found 620.3169.

(Preparation of Compound III)

A DMF solution (20 mL) of adipic acid (1.0 g, 6.84 mmol) was stirred, and N-hydroxysuccinimide (3.0 g, 27.4 mmol) and EDC (5.14 g, 27.4 mmol) were added. After stirring the solution at room temperature for 24 hours, the reaction mixture was concentrated under reduced pressure, the crude product was dissolved in 200 mL of acetone, and 250 mL of 1 M hydrochloric acid aqueous solution was added dropwise. After 2 hours, white precipitate was filtered, and washed with water and acetone to obtain the target substance (1.75 g, 77%). $^1$H NMR (500 MHz, CDCl$_3$, 25° C.) δ2.84 (s, 4H), 2.83 (s, 4H), 2.67 (t, J=3.5 Hz, 4H), 1.89 (t, J=3.5 Hz, 4H); $^{13}$C NMR (125 MHz, CDCl$_3$, 25° C.) 169.4, 168.4, 30.7, 25.9, 23.9. ESI-HRMS m/z calcd for C$_{14}$H$_{17}$N$_2$O$_8$ ([M+H]$^+$) 341.0979, found 341.0973.

(Preparation of Compound IV)

A DMF solution (680 mL) of compound II (28.8 mg, 0.034 mmol) and compound III (23.2 mg, 0.068 mmol) was stirred, and DIEA (16.8 μL, 0.10 mmol) was added. After stirring the solution at room temperature for 24 hours, and the mixture was directly purified with a reverse phase HPLC with the same condition as that employed in the preparation of compound I to obtain the target compound (14.0 mg, 43%). $^1$H NMR (500 MHz, CD$_3$OD, 25° C.) δ7.00 (d, J=6.5 Hz, 2H), 6.68 (d, J=6.5 Hz, 2H), 4.74 (t, J=7.0 Hz, 1H), 4.41 (q, J=7.0 Hz, 1H), 4.26-4.30 (m, 2H), 3.91-3.86 (m, 1H), 3.22-3.18 (m, 1H), 3.14-3.10 (m, 1H), 3.09 (t, J=6.5 Hz, 2H), 2.91-2.85 (m, 2H), 2.84-2.78 (m, 5H), 2.59 (t, J=9.5 Hz, 2H), 2.64-2.60 (m, 1H), 2.58 (dd, J=16.5, 9.0 Hz, 1H), 2.19 (t, J=7.0 Hz, 2H), 2.22 (t, J=7.0 Hz, 2H), 1.92-1.82 (m, 1H), 1.74-1.60 (m, 6H), 1.57-1.44 (m, 3H), 1.44-1.32 (m, 2H), 1.09-0.90 (m, 2H); ESI-HRMS m/z calcd for C$_{37}$H$_{53}$N$_{10}$O$_{13}$ ([M+H]$^+$) 845.3788, found 845.3769.

(Preparation of cRGD-PE)

A DMF solution (200 μL) of compound IV (4.2 mg, 3.9 μmol) and compound V (1.1 mg, 7.8 μmol) was stirred, and DIEA (3.3 μL, 19.6 μmol) was added. After stirring the solution at room temperature for 24 hours, the mixture was directly purified with a reverse phase HPLC with the same condition as that employed in the preparation of compound I to obtain cRGD-PE (3.2 mg, 85%). δ$^1$H NMR (500 MHz, CD$_3$OD, 25° C.) 7.02 (d, J=7.0 Hz, 2H), 6.71 (d, J=7.0 Hz, 2H), 4.76 (t, J=7.5 Hz, 1H), 4.75 (s, 2H), 4.44 (t, J=7.5 Hz, 1H), 4.29-4.20 (m, 2H), 3.98 (s, 2H), 3.91 (dd, J=9.5, 3.0 Hz, 1H), 3.25-3.20 (m, 1H), 3.18-3.11 (m, 1H), 3.11 (t, J=7.0 Hz, 2H), 2.96 (s, 1H), 2.88 (d, J=8.0 Hz, 2H), 2.85 (dd, J=16.5, 8.0 Hz, 1H), 2.58 (dd, J=16.5, 8.0 Hz, 1H), 2.29 (t, J=7.0 Hz, 2H), 2.22 (t, J=7.0 Hz, 2H), 1.92-1.84 (m, 1H), 1.74-1.60 (m, 6H), 1.59-1.42 (m, 3H), 1.41 (t, J=8.0 Hz, 2H), 1.09-0.80 (m, 2H); ESI-HRMS m/z calcd for C$_{38}$H$_{55}$N$_{10}$O$_{12}$ ([M+H]$^+$) 843.3995, found 843.4006.

8-2. Preparation of GArM Complex

Using a previously reported method, a sugar chain-aldehyde probe having a terminal α(2,3)-sialic acid (R. Sibgatullina, K. Fujiki, T. Murase, T. Yamamoto, T. Shimoda, A. Kurbangalieva, K. Tanaka, Highly reactive "RIKEN click" probe for glycoconjugation on lysines. Tetrahedron Lett. 58, 1929-1933 (2017).), as well as a gold catalyst bound to coumarin (K. Tsubokura, K. K. Vong, A. R. Pradipta, A. Ogura, S. Urano, T. Tahara, S. Nozaki, H. Onoe, Y. Nakao, R. Sibgatullina, A. Kurbangalieva, Y. Watanabe, K. Tanaka, In vivo gold complex catalysis within live mice. Angew. Chem. Int. Ed. 56, 3579-3584 (2017).) were synthesized.

To a human serum albumin solution (5.3 mL of aqueous solution, 66.7 nmol), a solution of a sugar chain-aldehyde probe having a terminal α(2,3)-sialic acid in DMSO (1 μmol, 15 equivalents, 260 μL from 3.8 mM stock solution) was added under atmosphere. The solution was gently stirred, and incubated overnight at 37° C. Subsequently, the solution was concentrated with Amicon Ultra Centrifugal filter (30 kDa), and washed with water. After removing the insoluble byproduct with Durapore membrane (Durapore PVDF 0.45 μm™), water was added for dilution to obtain 1.0 mM stock solution of sugar chain albumin. Confirmation of the number of bound sugar chains was performed with MALDI-TOF-MS (positive mode), and the molecular weight of sugar chain albumin having 6.2 molecules of sugar chains bound per 1 molecule of albumin was thereby detected (85.8 kDa). In the next step of the protocol, to a solution of sugar chain albumin solution (66.7 nmol) in PBS buffer (60.6 μL, pH 7.4), a solution of coumarin-gold complex (66.7 nmol) in DMSO (6.1 μL) was added. The solution was gently stirred and incubated at 37 degrees for 1 hour, after which the solution was concentrated with Amicon Ultra Centrifugal filter (30 kDa), and washed with PBS buffer solution to obtain the target GArM complex.

(Cells)

Because HeLa cancer cells are known to overexpress RGD-specific integrins ($\alpha_5\beta_1$, $\alpha v\beta_3$, $\alpha v\beta_5$), HeLa cells were selected as the model in this research. HeLa cells employed were provided from the Cell Engineering Division—CELL BANK—at RIKEN.

HeLa cells were cultured in Dulbecco modified Eagle's medium (DMEM) supplemented with 10% heat inactivated fetal bovine serum (FBS) and 1% penicillin-streptomycin. HeLa-Luc cell strain was made by stable transfection of HeLa cells by firefly luciferase and puromycin acetyl transferase cultured in DMEM comprising 10% FBS and 0.01% puromycin. HeLa-V cell strain was made by stable transfection of HeLa cells by firefly luciferase and Venus (V) cultured in DMEM comprising 10% FBS, 1% penicillin-streptomycin, and 0.8% Geneticin. All cell strains were allowed to propagate in an incubator at 37° C. containing 5% carbon dioxide. As previously described (A. Ray, B. N. Dittel, Isolation of mouse peritoneal cavity cells. JoVE, e1488 723 (2010).), mouse macrophage was collected from the peritoneal cavity of BALB/c-nu/nu mice administered with 0.9% saline (6 mL).

8-3. Verification of Selectivity of GArM Towards HeLa Cell

In order to confirm whether GArM can more selectively target HeLa cells, a series of flow cytometry research was performed. Since the fluorescence intensity of coumarin derivative in known to increase when bound to albumin, fluorescence intensity measured in flow cytometry at $\lambda_{Ex}$=405 nm/$\lambda_{Em}$=470 nm will be an indicator of whether the coumarin-bound GArM complex bound to the cells.

Flow cytometry and cell sorting was performed with Sony SH800 Cell Sorter (Sony Corporation) by a common method. The flow cytometer was equipped with 405, 488, 561, and 638 nm lasers, excitation/emission wavelength gates of $\lambda_{Ex}$=405 nm/$\lambda_{Em}$=470 nm for GArM detection and $\lambda_{Ex}$=515 nm/$\lambda_{Em}$=528 nm for Venus (V) detection were each employed, and the result was analyzed with Sony SH800 software.

Figure 18:
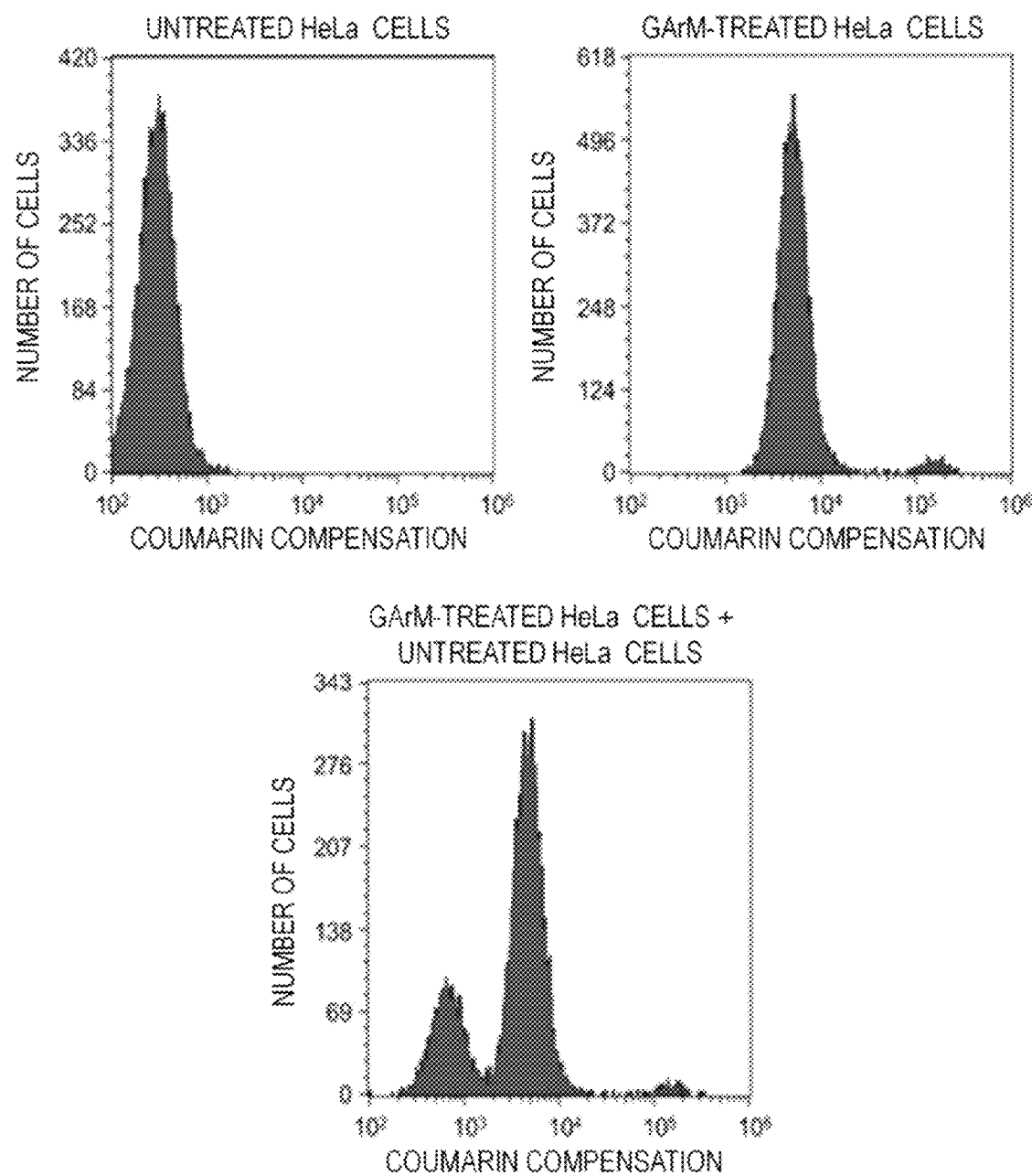
FIG. 18 shows the comparison of flow cytometry results of GArM-treated HeLa cells and untreated HeLa cells.

First, in the cell culture system, an apparent difference in peak was seen in flow cytometry between GArM-treated HeLa cells and untreated HeLa cells (FIG. 18). By mixing GArM-treated HeLa cells and untreated HeLa cells, this characteristic was emphasized more, and peaks that are clearly defined as two peaks were seen.

Figure 19:
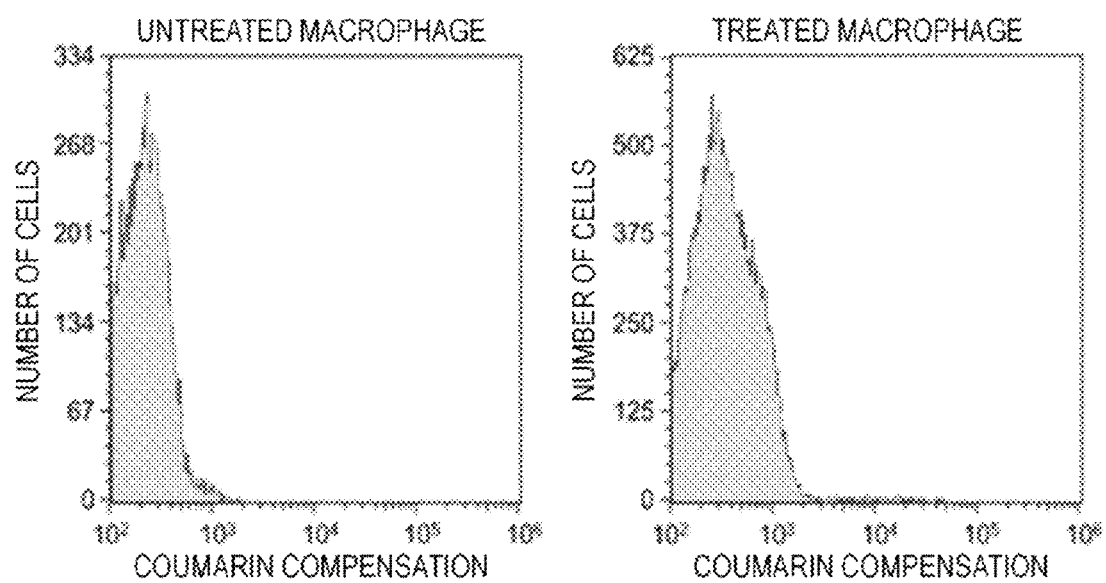
FIG. 19 shows the comparison of flow cytometry results of GArM-treated mouse peritoneal cavity-derived macrophages and untreated mouse peritoneal cavity-derived macrophages.

Next, as a control experiment, the binding ability of GArM was examined with macrophages extracted from the peritoneal cavity of mice. Comparing the flow cytometry histogram (FIG. 19), only a slight difference was observed between macrophages with and without addition of GArM, and this, as anticipated, suggests that there is no or almost no binding.

Figure 20:
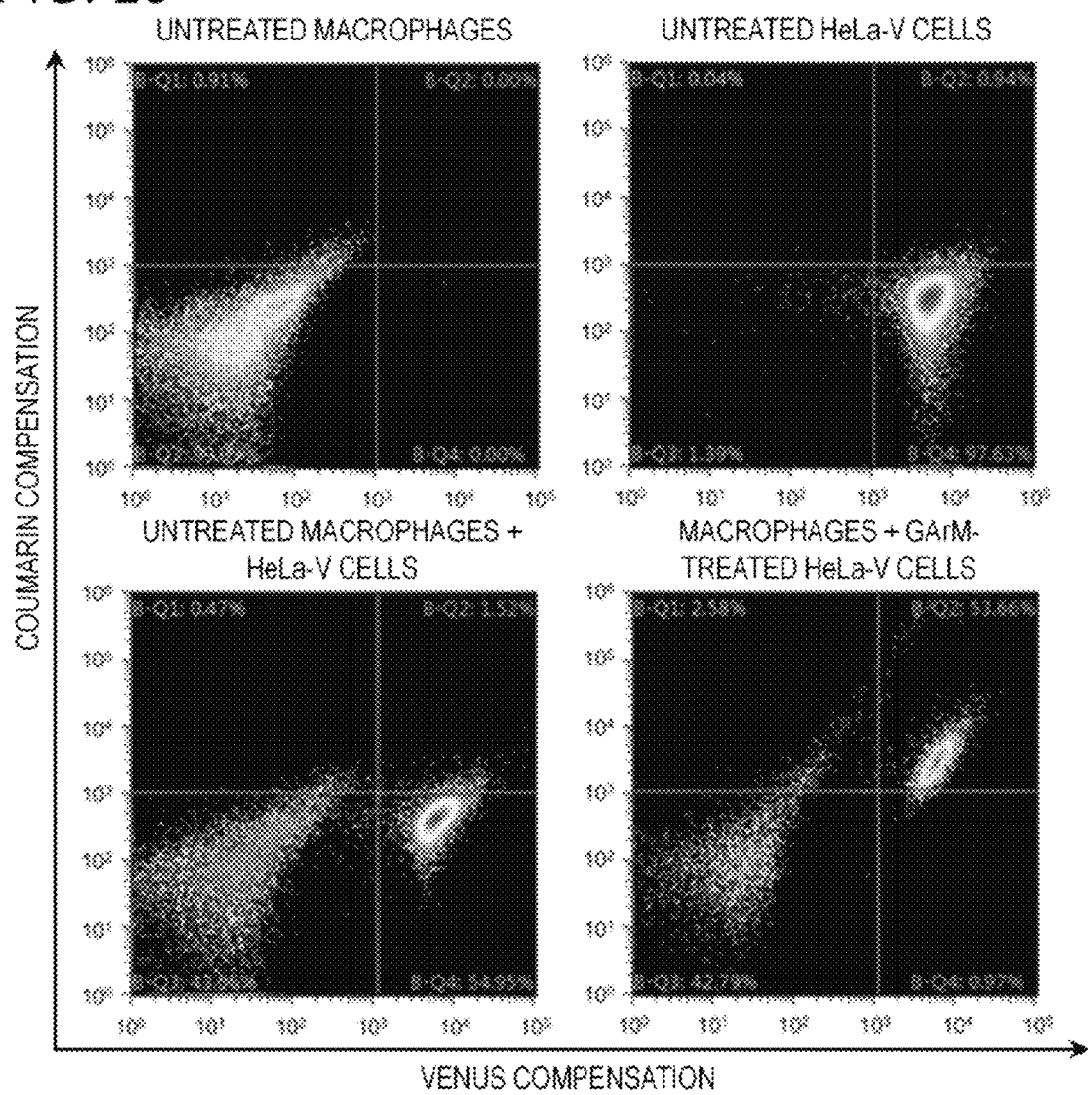
FIG. 20 shows the comparison of flow cytometry results of HeLa cells and mouse peritoneal cavity-derived macrophages treated with GArM, as well as HeLa cells and mouse peritoneal cavity-derived macrophages not treated with GArM. Note that the Q3 values of the upper left and the bottom left figures are 99.09% and 43.06%, respectively.

In a final test that verifies selectivity, the combinations of macrophage and HeLa cells incubated with or without addition of GArM were observed (FIG. 20). In this experiment, in order to observe HeLa cells and macrophage with discrimination, HeLa-V cell strain expressing Venus (V) yellow fluorescent protein was used. From the flow cytometry profile, Venus-expressing HeLa cells and macrophages can be clearly discriminated. It was found that when GArM is added, the majority of the HeLa-V cells migrate to the top right portion which shows GArM binding. On the other hand, such change was not seen with macrophages. As a result, this data strongly indicates that GArM can preferentially bind to HeLa cancer cells at the cell level.

8-4. Cell Adhesion Assay

The ability of SeCT labeling reagent (GArM/cRGD-PE) that impedes cell adhesion based on integrin was confirmed by in vitro cell adhesion assay. Cell adhesion assay was performed with Human Fibronectin Coated 96-Well Microplates purchased from R&D System (Minneapolis, U.S.A.).

The adhered cells were quantified with a commercially available MTS assay CellTiter 96 Aqueous One Solution cell proliferation assay (Promega). HeLa cells employed in this experiment were made serum free 16 hours before the experiment by exchanging the proliferation medium to DMEM (serum-free). Subsequently, cells were subcultured to a concentration of $6 \times 10^5$ call/mL stock solution, and the remaining trypsin was removed by further centrifugation. Next, a mixed solution was prepared in an Eppendorf tube with HeLa cells (360 µL from cell stock solution), cRGD-PE (45 µL from 0, 160, 320, 640, 1280, 2560, 5120, 10240 µM stock aqueous solution), and GArM (45 µL from 400 µM PBS buffer solution). In parallel, GArM is substituted to 45 µL of PBS buffer solution only to prepare a control solution. Incubation was performed at room temperature for 1 hour with a rocking shaker. Next, a washing step of spinning down the cells (at 0.8 ppm for 4 minutes) and removing the supernatant fluid, and then resuspending in 450 µL of DMEM only (serum-free) was performed two times. In a fibronectin-coated 96-well microplate, 130 µL of labeled HeLa cell mixture was added to each well, and subsequently, this plate was incubated at 37° C. for 10 minutes. After removing the medium, the adhered cells were washed 3-4 times with PBS buffer solution. PBS buffer solution was intermittently pipetted up and down in order to remove non-specifically bound cells. In the final step, 100 µL of DMEM (10% FBS+1% penicillin-streptomycin) and 20 µL of MTS reagent were added. After incubating at 37° C. for 4 hours, the endpoint absorbance at 490 nm was obtained with SpectraMax iD3 multi-mode microplate reader (Molecular Devises, U.S.A.).

Figure 21:
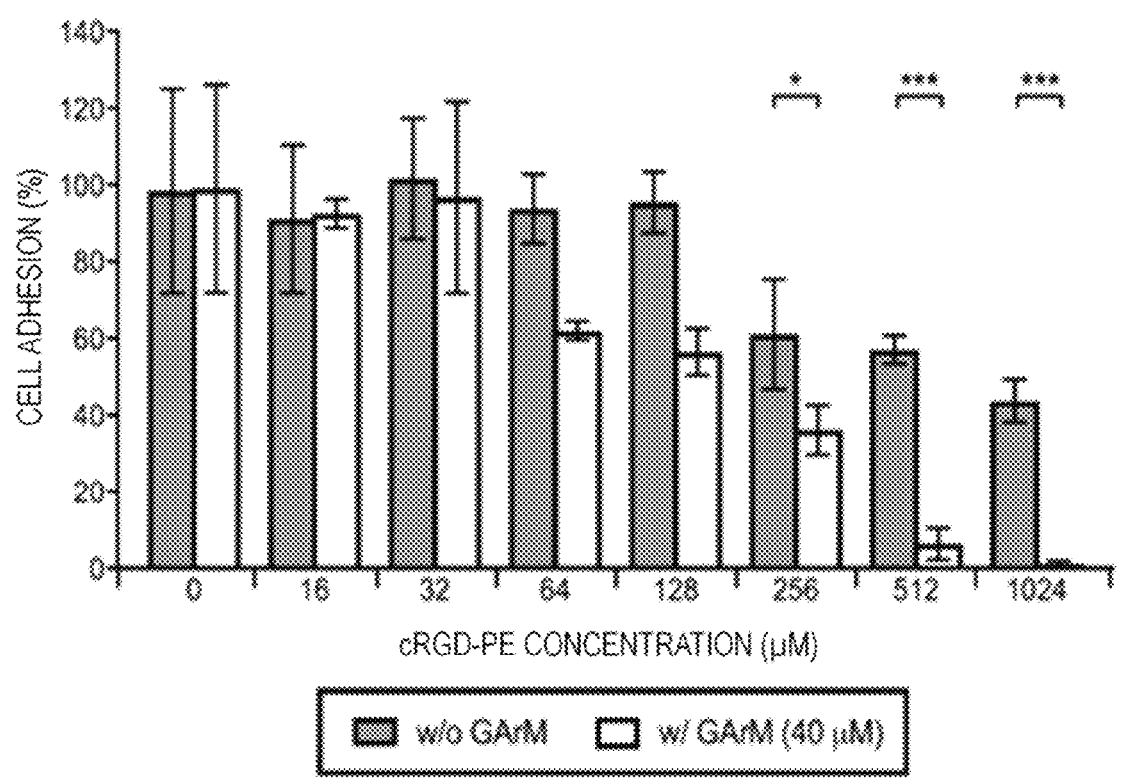
FIG. 21 show the result of cell adhesion assay performed in Example 8.

The result is shown in FIG. 21. As anticipated, a significant difference in cell adhesion on fibronectin-coated plates was observed for HeLa cells treated with SeCT labeling reagent (GArM/cRGD-PE). These differences were in particular more apparent when the cRGD-PE treatment concentration is high, and this indicates that cRGD catalytically bound on the cell surface has a higher concentration.

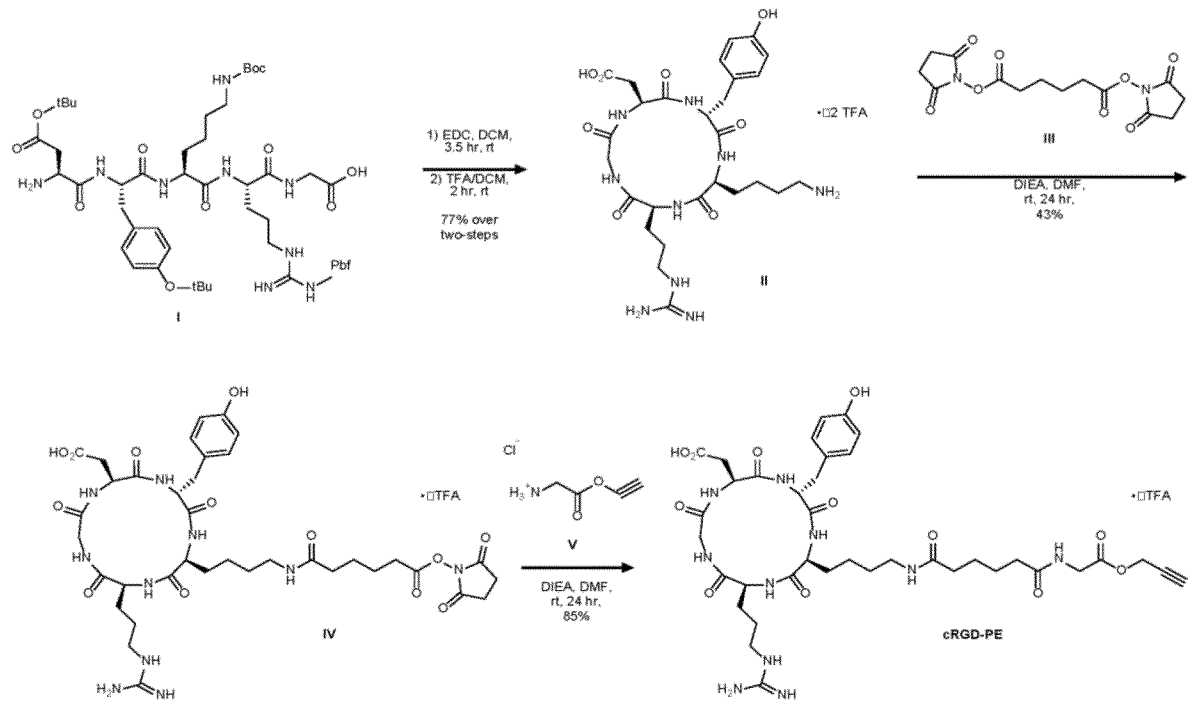

The invention claimed is:

1. A complex of a protein and a catalyst selected from metal catalysts or organic catalysts, wherein
    said protein is a protein that has a hydrophobic pocket within its three-dimensional structure, and
    said complex accommodates said catalyst in said hydrophobic pocket so that said catalyst is not exposed or not substantially exposed to a hydrophilic environment.

2. The complex according to claim 1, wherein said protein is selected from the group consisting of human serum albumin (HSA), immunoglobulin G (IgG), immunoglobulin A (IgA), transferrin, antitrypsin, haptoglobin, α1-acidic glycoprotein, Myoferlin, Trk receptor, estrogen receptor, and folate receptor.

3. The complex according to claim 1, wherein said metal catalyst is selected from the group consisting of a boron catalyst, a magnesium catalyst, an aluminum catalyst, a silicon catalyst, a calcium catalyst, a scandium catalyst, a titanium catalyst, a vanadium catalyst, a chromium catalyst, a manganese catalyst, an iron catalyst, a cobalt catalyst, a nickel catalyst, a copper catalyst, a zinc catalyst, an yttrium catalyst, a zirconium catalyst, a niobium catalyst, a molybdenum catalyst, a ruthenium catalyst, a rhodium catalyst, a palladium catalyst, a silver catalyst, an indium catalyst, a tin catalyst, a barium catalyst, a hafnium catalyst, a tungsten catalyst, a rhenium catalyst, an osmium catalyst, an iridium catalyst, a platinum catalyst, a gold catalyst, and a lanthanoid Lewis acid catalyst.

4. The complex according to claim 1, wherein
    said protein is a human serum albumin, and
    said catalyst is a metal catalyst.

5. The complex according to claim 4, wherein said metal catalyst is a ruthenium catalyst.

6. The complex according to claim 5, wherein said hydrophobic pocket of the human serum albumin is albumin drug binding site I (drug site I).

7. The complex according to claim 4, wherein said hydrophobic pocket of the human serum albumin is albumin drug binding site I (drug site I).

8. The complex according to claim 4, wherein said metal catalyst is bound to the said hydrophobic pocket via a ligand against human serum albumin.

9. The complex according to claim 8, wherein said ligand is selected from the group consisting of warfarin, azapropazone, acenocoumarol, phenylbutazone, salicylate salt, indomethacin, phenytoin, tolbutamide, chlorpropamide, iophenoxate, iodipamide, sulfadimethoxine, phenprocoumon, glibenclamide, sulfathiazole, tenoxicam, camptothecin, prodan, bilirubin, eicosanoid, and carboxy-methylpropyl-furanpropanoate (uremic toxin), and coumarin.

10. The complex according to claim 8, wherein said metal catalyst is bound to the said hydrophobic pocket via a linker bound to said ligand.

11. The complex according to claim 1, wherein the surface of said protein is modified so as to interact with a target site in vivo.

12. The complex according to claim 11, wherein said modification is a modification by a sugar chain.

13. The complex according to claim 1, wherein said protein further comprises a portion that interacts with a target site in vivo.

14. A composition comprising the complex according to claim 1.

15. The composition according to claim 14, which is a pharmaceutical composition further comprising a pharmaceutically acceptable carrier.

16. The composition according to claim 15, which is used in combination with a prodrug, wherein the prodrug is activated by said complex.

17. The composition according to claim 15, wherein said composition is adapted to selectively tag particular cells.

18. The composition according to claim 17, wherein the particular cells comprise a chemical substance that is tagged to said cells.

19. A pharmaceutical composition comprising a prodrug, wherein said prodrug is adapted to be activated by the complex according to claim 1, and said pharmaceutical composition is used in combination with the complex.

20. A combination medicine comprising:
a first agent comprising the complex according to claim 1, and
a second agent comprising a prodrug adapted to be activated by said complex.

* * * * *

UNITED STATES PATENT AND TRADEMARK OFFICE
CERTIFICATE OF CORRECTION

Page 1 of 2

PATENT NO. : 12,269,021 B2
APPLICATION NO. : 17/612780
DATED : April 8, 2025
INVENTOR(S) : Tanaka et al.

It is certified that error appears in the above-identified patent and that said Letters Patent is hereby corrected as shown below:

In the Specification

Columns 13-14, Chemical Formula 1: Please delete and replace with the following:

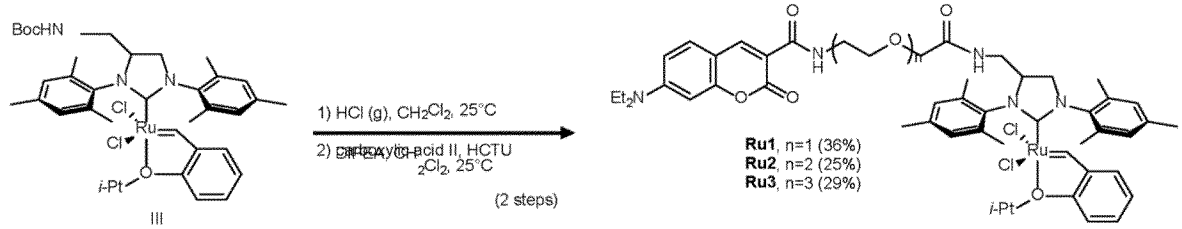

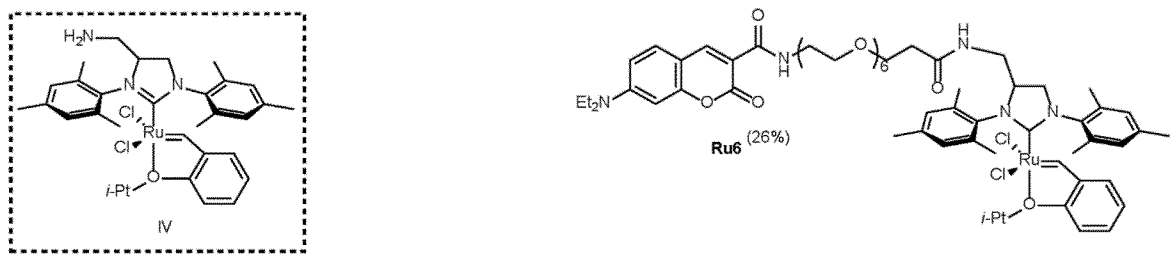

Column 15, Line 18: Please correct "Rul" to read --Ru1--

Column 16, Line 5: Please correct "Rul" to read --Ru1--

Column 19, Line 27: Please correct "Rul" to read --Ru1--

Column 21, Line 9: Please correct "Rul" to read --Ru1--

Column 22, Line 40: Please correct "(e.g. Rul)" to read --(e.g. Ru1)--

Signed and Sealed this
Fifteenth Day of July, 2025

Coke Morgan Stewart
*Acting Director of the United States Patent and Trademark Office*

CERTIFICATE OF CORRECTION (continued)
U.S. Pat. No. 12,269,021 B2

Column 23, Line 34: Please correct "Rul" to read --Ru1--

Column 23, Line 42: Please correct "Rul" to read --Ru1--

Column 24, Line 61: Please correct "1H" to read --1h--

Column 25, Line 4: Please correct "GArM-Rul" to read --GArM-Ru1--

Column 25, Line 26: Please correct "GArM-Rul" to read --GArM-Ru1--

Column 25, Line 28: Please correct "GArM-Rul" to read --GArM-Ru1--

Column 25, Lines 65-66: Please remove the paragraph break between "solution." and "Water"

Columns 29-30 - Columns 31-32, Chemical Formula 9: Please delete and replace with the following: